(12) United States Patent
Ortiz et al.

(10) Patent No.: US 8,187,163 B2
(45) Date of Patent: May 29, 2012

(54) METHODS FOR IMPLANTING A GASTRIC RESTRICTION DEVICE

(75) Inventors: Mark S. Ortiz, Milford, OH (US); Daniel F. Dlugos, Jr., Middletown, OH (US); Amy L. Marcotte, Mason, OH (US); Randal T. Byrum, South Lebanon, OH (US); Kevin Doll, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1204 days.

(21) Appl. No.: 11/953,504

(22) Filed: Dec. 10, 2007

(65) Prior Publication Data

US 2009/0149874 A1 Jun. 11, 2009

(51) Int. Cl.
*A61M 5/00* (2006.01)
*A61M 31/00* (2006.01)

(52) U.S. Cl. .......................................................... 600/37
(58) Field of Classification Search .................... 600/37; 606/151–158; 604/288.01–288.04
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |

(Continued)

FOREIGN PATENT DOCUMENTS

CA 1059035 7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Charles A Marmor, II
*Assistant Examiner* — Catherine E Burk
(74) *Attorney, Agent, or Firm* — Nutter McClennen & Fish LLP

(57) ABSTRACT

Various exemplary methods are disclosed for implanting a restriction device for forming a restriction in a patient. The methods can be used with a variety of restriction devices, but in an exemplary embodiment the methods are used for implanting a gastric restriction device.

21 Claims, 17 Drawing Sheets

U.S. PATENT DOCUMENTS

| | | |
|---|---|---|
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |
| 3,240,510 A | 3/1966 | Spouge |

| | | | | | | |
|---|---|---|---|---|---|---|
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |
| 3,482,816 A | 12/1969 | Arnold | | 3,731,681 A | 5/1973 | Blackshear et al. |
| 3,487,959 A | 1/1970 | Pearne et al. | | 3,732,731 A | 5/1973 | Fussell, Jr. |
| 3,491,842 A | 1/1970 | Delacour et al. | | 3,735,040 A | 5/1973 | Punt et al. |
| 3,492,638 A | 1/1970 | Lane | | 3,736,930 A | 6/1973 | Georgi |
| 3,502,829 A | 3/1970 | Reynolds | | 3,738,356 A | 6/1973 | Workman |
| 3,503,116 A | 3/1970 | Strack | | 3,740,921 A | 6/1973 | Meyer et al. |
| 3,504,664 A | 4/1970 | Haddad | | 3,746,111 A | 7/1973 | Berthiaume et al. |
| 3,505,808 A | 4/1970 | Eschle | | 3,748,678 A | 7/1973 | Ballou |
| 3,509,754 A | 5/1970 | Massingill et al. | | 3,749,098 A | 7/1973 | De Bennetot et al. |
| 3,512,517 A | 5/1970 | Kadish et al. | | 3,749,422 A | 7/1973 | Abildgaard et al. |
| 3,514,919 A | 6/1970 | Ashton et al. | | 3,749,423 A | 7/1973 | Abildgaard et al. |

| | | |
|---|---|---|
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |
| 4,045,345 A | 8/1977 | Drori et al. |
| 4,047,851 A | 9/1977 | Bender |
| 4,048,494 A | 9/1977 | Liesting et al. |
| 4,048,879 A | 9/1977 | Cox |
| 4,049,004 A | 9/1977 | Walters |
| 4,051,338 A | 9/1977 | Harris, III |
| 4,052,991 A | 10/1977 | Zacouto et al. |
| 4,055,074 A | 10/1977 | Thimons et al. |
| 4,055,175 A | 10/1977 | Clemens et al. |

| | | | | | |
|---|---|---|---|---|---|
| 4,056,854 A | 11/1977 | Boretos et al. | 4,192,192 A | 3/1980 | Schnell |
| 4,058,007 A | 11/1977 | Exner et al. | 4,193,397 A | 3/1980 | Tucker et al. |
| 4,062,351 A | 12/1977 | Hastwell et al. | 4,204,547 A | 5/1980 | Allocca |
| 4,062,354 A | 12/1977 | Taylor et al. | 4,206,755 A | 6/1980 | Klein et al. |
| 4,062,360 A | 12/1977 | Bentley | 4,206,761 A | 6/1980 | Cosman |
| 4,063,439 A | 12/1977 | Besson et al. | 4,206,762 A | 6/1980 | Cosman |
| 4,064,882 A | 12/1977 | Johnson et al. | 4,207,903 A | 6/1980 | O'Neill |
| 4,070,239 A | 1/1978 | Bevilacqua | 4,212,074 A | 7/1980 | Kuno et al. |
| 4,072,047 A | 2/1978 | Reismuller et al. | 4,217,221 A | 8/1980 | Masso |
| 4,073,292 A | 2/1978 | Edelman | 4,217,588 A | 8/1980 | Freeny, Jr. |
| 4,075,099 A | 2/1978 | Pelton et al. | 4,220,189 A | 9/1980 | Marquez |
| 4,075,602 A | 2/1978 | Clothier | 4,221,219 A | 9/1980 | Tucker |
| 4,077,072 A | 3/1978 | Dezura et al. | 4,221,523 A | 9/1980 | Eberle |
| 4,077,394 A | 3/1978 | McCurdy | 4,223,837 A | 9/1980 | Gubbiotti et al. |
| 4,077,405 A | 3/1978 | Haerten et al. | 4,226,124 A | 10/1980 | Kersten et al. |
| 4,077,882 A | 3/1978 | Gangemi | 4,226,229 A | 10/1980 | Eckhart et al. |
| 4,078,620 A | 3/1978 | Westlake et al. | 4,227,533 A | 10/1980 | Godfrey |
| 4,080,653 A | 3/1978 | Barnes, Jr. et al. | 4,231,376 A | 11/1980 | Lyon et al. |
| 4,084,752 A | 4/1978 | Hagiwara et al. | 4,232,682 A | 11/1980 | Veth |
| 4,086,488 A | 4/1978 | Hill | 4,237,900 A | 12/1980 | Schulman et al. |
| 4,087,568 A | 5/1978 | Fay et al. | 4,241,247 A | 12/1980 | Byrne et al. |
| 4,088,417 A | 5/1978 | Kosmowski | 4,241,870 A | 12/1980 | Marcus |
| 4,089,329 A | 5/1978 | Couvillon, Jr. et al. | 4,245,593 A | 1/1981 | Stein |
| 4,090,802 A | 5/1978 | Bilz et al. | 4,246,877 A | 1/1981 | Kennedy |
| 4,092,719 A | 5/1978 | Salmon et al. | 4,247,850 A | 1/1981 | Marcus |
| 4,092,925 A | 6/1978 | Fromson | 4,248,238 A | 2/1981 | Joseph et al. |
| 4,096,866 A | 6/1978 | Fischell | 4,248,241 A | 2/1981 | Tacchi |
| 4,098,293 A | 7/1978 | Kramer et al. | 4,256,094 A | 3/1981 | Kapp et al. |
| 4,103,496 A | 8/1978 | Colamussi et al. | 4,256,118 A | 3/1981 | Nagel et al. |
| 4,106,370 A | 8/1978 | Kraus et al. | 4,262,343 A | 4/1981 | Claycomb |
| 4,107,689 A | 8/1978 | Jellinek | 4,262,632 A | 4/1981 | Hanton et al. |
| 4,107,995 A | 8/1978 | Ligman et al. | 4,265,241 A | 5/1981 | Portner et al. |
| 4,108,148 A | 8/1978 | Cannon, III | 4,265,252 A | 5/1981 | Chubbuck et al. |
| 4,108,575 A | 8/1978 | Schal | 4,271,018 A | 6/1981 | Drori et al. |
| 4,109,148 A | 8/1978 | Jaulmes et al. | 4,273,070 A | 6/1981 | Hoefelmayr et al. |
| 4,109,518 A | 8/1978 | Dooley et al. | 4,274,444 A | 6/1981 | Ruyak |
| 4,109,644 A | 8/1978 | Kojima | 4,275,600 A | 6/1981 | Turner et al. |
| 4,111,056 A | 9/1978 | Mastromatteo | 4,275,913 A | 6/1981 | Marcus |
| 4,111,629 A | 9/1978 | Nussbaumer et al. | 4,278,540 A | 7/1981 | Drori et al. |
| 4,114,424 A | 9/1978 | Johnson | 4,280,036 A | 7/1981 | Fukatsu et al. |
| 4,114,606 A | 9/1978 | Seylar | 4,280,775 A | 7/1981 | Wood |
| 4,120,097 A | 10/1978 | Jeter | 4,281,666 A | 8/1981 | Cosman |
| 4,120,134 A | 10/1978 | Scholle | 4,281,667 A | 8/1981 | Cosman |
| 4,121,635 A | 10/1978 | Hansel | 4,284,073 A | 8/1981 | Krause et al. |
| 4,123,310 A | 10/1978 | Varon et al. | 4,285,770 A | 8/1981 | Chi et al. |
| 4,124,023 A | 11/1978 | Fleischmann et al. | 4,291,699 A | 9/1981 | Geddes et al. |
| 4,127,110 A | 11/1978 | Bullara | 4,295,963 A | 10/1981 | Drori et al. |
| 4,130,169 A | 12/1978 | Denison | 4,297,927 A | 11/1981 | Kuroda et al. |
| 4,131,596 A | 12/1978 | Allen | 4,303,075 A | 12/1981 | Heilman et al. |
| 4,133,355 A | 1/1979 | Mayer | 4,305,402 A | 12/1981 | Katims |
| 4,133,367 A | 1/1979 | Abell | 4,312,374 A | 1/1982 | Drori et al. |
| 4,140,131 A | 2/1979 | Dutcher et al. | 4,314,480 A | 2/1982 | Becker |
| 4,141,348 A | 2/1979 | Hittman | 4,316,693 A | 2/1982 | Baxter et al. |
| 4,141,349 A | 2/1979 | Ory et al. | 4,325,387 A | 4/1982 | Helfer |
| 4,143,661 A | 3/1979 | LaForge et al. | 4,327,804 A | 5/1982 | Reed |
| 4,146,029 A | 3/1979 | Ellinwood, Jr. | 4,328,654 A | 5/1982 | Van Ginkel et al. |
| 4,147,161 A | 4/1979 | Ikebe et al. | 4,332,254 A | 6/1982 | Lundquist |
| 4,148,096 A | 4/1979 | Haas et al. | 4,339,831 A | 7/1982 | Johnson |
| 4,149,423 A | 4/1979 | Frosch et al. | 4,342,218 A | 8/1982 | Fox |
| 4,151,823 A | 5/1979 | Grosse et al. | 4,342,308 A | 8/1982 | Trick |
| 4,153,085 A | 5/1979 | Adams | 4,346,604 A | 8/1982 | Snook et al. |
| 4,156,422 A | 5/1979 | Hildebrandt et al. | 4,347,851 A | 9/1982 | Jundanian |
| 4,160,448 A | 7/1979 | Jackson | 4,350,647 A | 9/1982 | de la Cruz |
| 4,160,971 A | 7/1979 | Jones et al. | 4,350,970 A | 9/1982 | von Tomkewitsch et al. |
| 4,166,469 A | 9/1979 | Littleford | 4,351,037 A | 9/1982 | Scherbatskoy |
| 4,167,304 A | 9/1979 | Gelbke | 4,351,116 A | 9/1982 | Scott, Jr. |
| 4,167,952 A | 9/1979 | Reinicke | 4,356,486 A | 10/1982 | Mount |
| 4,168,567 A | 9/1979 | Leguy et al. | 4,360,010 A | 11/1982 | Finney |
| 4,170,280 A | 10/1979 | Schwarz | 4,360,277 A | 11/1982 | Daniel et al. |
| 4,171,218 A | 10/1979 | Hoshino et al. | 4,361,153 A | 11/1982 | Slocum et al. |
| 4,183,124 A | 1/1980 | Hoffman | 4,363,236 A | 12/1982 | Meyers |
| 4,183,247 A | 1/1980 | Allen et al. | 4,364,276 A | 12/1982 | Shimazoe et al. |
| 4,185,641 A | 1/1980 | Minior et al. | 4,365,425 A | 12/1982 | Gotchel |
| 4,186,287 A | 1/1980 | Scott | 4,368,937 A | 1/1983 | Palombo et al. |
| 4,186,749 A | 2/1980 | Fryer | 4,369,013 A | 1/1983 | Abildgaard et al. |
| 4,186,751 A | 2/1980 | Fleischmann | 4,373,527 A | 2/1983 | Fischell |
| 4,190,057 A | 2/1980 | Hill et al. | 4,376,523 A | 3/1983 | Goyen et al. |
| 4,191,004 A | 3/1980 | Gmuer et al. | 4,378,809 A | 4/1983 | Cosman |
| 4,191,187 A | 3/1980 | Wright et al. | 4,380,427 A | 4/1983 | Hehl et al. |

| Patent No. | Date | Name |
|---|---|---|
| 4,385,636 A | 5/1983 | Cosman |
| 4,386,422 A | 5/1983 | Mumby et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,408,615 A | 10/1983 | Grossman |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush et al. |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,552,150 A | 11/1985 | Zacouto et al. |
| 4,553,226 A | 11/1985 | Scherbatskoy |
| 4,556,063 A | 12/1985 | Thompson et al. |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,596,563 A | 6/1986 | Pande |
| 4,599,943 A | 7/1986 | Kobler et al. |
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,617,016 A | 10/1986 | Blomberg et al. |
| 4,618,861 A | 10/1986 | Gettens et al. |
| 4,620,807 A | 11/1986 | Polit |
| 4,621,331 A | 11/1986 | Iwata et al. |
| 4,622,871 A | 11/1986 | Van Sickle et al. |
| 4,626,462 A | 12/1986 | Kober et al. |
| 4,633,304 A | 12/1986 | Nagasaki et al. |
| 4,633,878 A | 1/1987 | Bombardieri et al. |
| 4,635,182 A | 1/1987 | Hintz |
| 4,637,736 A | 1/1987 | Andeen et al. |
| 4,638,665 A | 1/1987 | Benson et al. |
| 4,644,246 A | 2/1987 | Knapen et al. |
| 4,646,553 A | 3/1987 | Tufte et al. |
| 4,648,363 A | 3/1987 | Kronich |
| 4,648,406 A | 3/1987 | Miller |
| 4,658,358 A | 4/1987 | Leach et al. |
| 4,658,760 A | 4/1987 | Zebuhr |
| 4,660,568 A | 4/1987 | Cosman |

| | | | | | |
|---|---|---|---|---|---|
| 4,665,511 A | 5/1987 | Rodney et al. | 4,812,823 A | 3/1989 | Dickerson |
| 4,665,896 A | 5/1987 | LaForge et al. | 4,819,656 A | 4/1989 | Spector |
| 4,669,484 A | 6/1987 | Masters | 4,820,265 A | 4/1989 | DeSatnick et al. |
| 4,672,974 A | 6/1987 | Lee | 4,820,953 A | 4/1989 | Saubolle et al. |
| 4,674,457 A | 6/1987 | Berger et al. | 4,821,167 A | 4/1989 | Wiebe |
| 4,674,546 A | 6/1987 | Fournier et al. | 4,821,723 A | 4/1989 | Baker, Jr. et al. |
| 4,678,408 A | 7/1987 | Nason et al. | 4,823,779 A | 4/1989 | Daly et al. |
| 4,681,559 A | 7/1987 | Hooven | 4,830,006 A | 5/1989 | Haluska et al. |
| 4,683,850 A | 8/1987 | Bauder et al. | 4,832,034 A | 5/1989 | Pizziconi et al. |
| 4,685,463 A | 8/1987 | Williams | 4,833,384 A | 5/1989 | Munro et al. |
| 4,685,469 A | 8/1987 | Keller et al. | 4,834,731 A | 5/1989 | Nowak et al. |
| 4,685,903 A | 8/1987 | Cable et al. | 4,838,857 A | 6/1989 | Strowe et al. |
| 4,686,987 A | 8/1987 | Salo et al. | 4,840,068 A | 6/1989 | Mayhew, Jr. |
| 4,687,530 A | 8/1987 | Berscheid et al. | 4,840,350 A | 6/1989 | Cook |
| 4,689,979 A | 9/1987 | Otsuka et al. | 4,844,002 A | 7/1989 | Yasui et al. |
| 4,691,694 A | 9/1987 | Boyd et al. | 4,846,153 A | 7/1989 | Berci |
| 4,691,710 A | 9/1987 | Dickens et al. | 4,846,191 A | 7/1989 | Brockway et al. |
| 4,693,253 A | 9/1987 | Adams | 4,846,664 A | 7/1989 | Hehl |
| 4,695,237 A | 9/1987 | Inaba et al. | 4,854,328 A | 8/1989 | Pollack |
| 4,696,189 A | 9/1987 | Hochreuther et al. | 4,863,470 A | 9/1989 | Carter |
| 4,697,574 A | 10/1987 | Karcher et al. | 4,865,587 A | 9/1989 | Walling |
| 4,698,038 A | 10/1987 | Key et al. | 4,867,160 A | 9/1989 | Schaldach et al. |
| 4,700,497 A | 10/1987 | Sato et al. | 4,867,498 A | 9/1989 | Delphia et al. |
| 4,700,610 A | 10/1987 | Bauer et al. | 4,867,618 A | 9/1989 | Brohammer |
| 4,701,143 A | 10/1987 | Key et al. | 4,869,252 A | 9/1989 | Gilli |
| 4,703,756 A | 11/1987 | Gough et al. | 4,870,258 A | 9/1989 | Mochizuki et al. |
| 4,705,507 A | 11/1987 | Boyles | 4,871,351 A | 10/1989 | Feingold et al. |
| 4,706,948 A | 11/1987 | Kroecher | 4,872,483 A | 10/1989 | Shah |
| 4,712,562 A | 12/1987 | Ohayon et al. | 4,872,869 A | 10/1989 | Johns |
| 4,718,425 A | 1/1988 | Tanaka et al. | 4,873,677 A | 10/1989 | Sakamoto et al. |
| 4,722,348 A | 2/1988 | Ligtenberg et al. | 4,875,483 A | 10/1989 | Vollmann et al. |
| 4,724,806 A | 2/1988 | Hartwig et al. | 4,880,004 A | 11/1989 | Baker, Jr. et al. |
| 4,724,830 A | 2/1988 | Fischell | 4,882,678 A | 11/1989 | Hollis et al. |
| 4,725,826 A | 2/1988 | Hunter | 4,886,392 A | 12/1989 | Iio et al. |
| 4,728,479 A | 3/1988 | Merkovsky | 4,895,151 A | 1/1990 | Grevis et al. |
| 4,729,517 A | 3/1988 | Krokor et al. | 4,896,594 A | 1/1990 | Baur et al. |
| 4,730,188 A | 3/1988 | Milheiser | 4,898,158 A | 2/1990 | Daly et al. |
| 4,730,420 A | 3/1988 | Stratmann et al. | 4,898,578 A | 2/1990 | Rubalcaba, Jr. |
| 4,730,619 A | 3/1988 | Koning et al. | 4,899,751 A | 2/1990 | Cohen |
| 4,731,058 A | 3/1988 | Doan | 4,899,752 A | 2/1990 | Cohen |
| 4,735,205 A | 4/1988 | Chachques et al. | 4,902,277 A | 2/1990 | Mathies et al. |
| 4,738,267 A | 4/1988 | Lazorthes et al. | 4,903,701 A | 2/1990 | Moore et al. |
| 4,738,268 A | 4/1988 | Kipnis | 4,909,678 A | 3/1990 | Kakimoto et al. |
| 4,741,345 A | 5/1988 | Matthews et al. | 4,913,147 A | 4/1990 | Fahlstrom et al. |
| 4,741,732 A | 5/1988 | Crankshaw et al. | 4,919,143 A | 4/1990 | Ayers |
| 4,743,129 A | 5/1988 | Keryhuel et al. | 4,924,872 A | 5/1990 | Frank |
| 4,745,541 A | 5/1988 | Vaniglia et al. | 4,926,903 A | 5/1990 | Kawai et al. |
| 4,746,830 A | 5/1988 | Holland | 4,932,406 A | 6/1990 | Berkovits |
| 4,750,495 A | 6/1988 | Moore et al. | 4,934,369 A | 6/1990 | Maxwell |
| 4,752,115 A | 6/1988 | Murray, Jr. et al. | 4,936,304 A | 6/1990 | Kresh et al. |
| 4,752,658 A | 6/1988 | Mack | 4,940,037 A | 7/1990 | Eckert et al. |
| 4,757,463 A | 7/1988 | Ballou et al. | 4,941,718 A | 7/1990 | Alexander, III et al. |
| 4,759,386 A | 7/1988 | Grouw, III | 4,942,004 A | 7/1990 | Catanzaro |
| 4,763,649 A | 8/1988 | Merrick | 4,944,050 A | 7/1990 | Shames et al. |
| 4,765,001 A | 8/1988 | Smith | 4,944,298 A | 7/1990 | Sholder |
| 4,767,406 A | 8/1988 | Wadham et al. | 4,944,307 A | 7/1990 | Hon et al. |
| 4,769,001 A | 9/1988 | Prince | 4,945,761 A | 8/1990 | Lessi et al. |
| 4,772,896 A | 9/1988 | Nakatsu et al. | 4,949,724 A | 8/1990 | Mahutte et al. |
| 4,773,401 A | 9/1988 | Citak et al. | 4,952,205 A | 8/1990 | Mauerer et al. |
| 4,774,950 A | 10/1988 | Cohen | 4,952,928 A | 8/1990 | Carroll et al. |
| 4,774,955 A | 10/1988 | Jones | 4,953,563 A | 9/1990 | Kaiser et al. |
| 4,777,953 A | 10/1988 | Ash et al. | 4,954,677 A | 9/1990 | Alberter et al. |
| 4,779,626 A | 10/1988 | Peel et al. | 4,958,630 A | 9/1990 | Rosenbluth et al. |
| 4,781,192 A | 11/1988 | Demer | 4,958,645 A | 9/1990 | Cadell et al. |
| 4,782,826 A | 11/1988 | Fogarty | 4,960,424 A | 10/1990 | Grooters |
| 4,783,106 A | 11/1988 | Nutter | 4,960,966 A | 10/1990 | Evans et al. |
| 4,788,847 A | 12/1988 | Sterghos | 4,967,585 A | 11/1990 | Grimaldo |
| 4,791,318 A | 12/1988 | Lewis et al. | 4,967,761 A | 11/1990 | Nathanielsz |
| 4,794,803 A | 1/1989 | Osterhout et al. | 4,970,823 A | 11/1990 | Chen et al. |
| 4,796,641 A | 1/1989 | Mills et al. | 4,971,251 A | 11/1990 | Dobrick et al. |
| 4,798,211 A | 1/1989 | Goor et al. | 4,977,896 A | 12/1990 | Robinson et al. |
| 4,798,227 A | 1/1989 | Goodwin | 4,978,335 A | 12/1990 | Arthur, III |
| 4,799,491 A | 1/1989 | Eckerle | 4,978,338 A | 12/1990 | Melsky et al. |
| 4,799,625 A | 1/1989 | Weaver, Jr. et al. | 4,979,730 A | 12/1990 | Holbrook et al. |
| 4,802,488 A | 2/1989 | Eckerle | 4,980,671 A | 12/1990 | McCurdy |
| 4,803,987 A | 2/1989 | Calfee et al. | 4,981,141 A | 1/1991 | Segalowitz |
| 4,804,368 A | 2/1989 | Skakoon et al. | 4,981,173 A | 1/1991 | Perkins et al. |
| 4,807,321 A | 2/1989 | Grasselli et al. | 4,981,426 A | 1/1991 | Aoki et al. |
| 4,808,167 A | 2/1989 | Mann et al. | 4,987,897 A | 1/1991 | Funke et al. |

| | | |
|---|---|---|
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |
| 5,298,884 A | 3/1994 | Gilmore et al. |
| 5,300,093 A | 4/1994 | Koestner et al. |
| 5,300,120 A | 4/1994 | Knapp et al. |

| | | | | | |
|---|---|---|---|---|---|
| 5,304,112 A | 4/1994 | Mrklas et al. | 5,513,945 A | 5/1996 | Hartmann et al. |
| 5,305,923 A | 4/1994 | Kirschner et al. | 5,514,103 A | 5/1996 | Srisathapat et al. |
| 5,312,443 A | 5/1994 | Adams et al. | 5,518,504 A | 5/1996 | Polyak |
| 5,312,452 A | 5/1994 | Salo | 5,520,606 A | 5/1996 | Schoolman et al. |
| 5,312,453 A | 5/1994 | Shelton et al. | 5,523,740 A | 6/1996 | Burgmann et al. |
| 5,313,953 A | 5/1994 | Yomtov et al. | 5,534,018 A | 7/1996 | Wahlstrand et al. |
| 5,314,451 A | 5/1994 | Mulier | 5,535,752 A | 7/1996 | Halperin et al. |
| 5,314,457 A | 5/1994 | Jeutter et al. | 5,538,005 A | 7/1996 | Harrison et al. |
| 5,324,315 A | 6/1994 | Grevious | 5,541,857 A | 7/1996 | Walter et al. |
| 5,325,834 A | 7/1994 | Ballheimer et al. | 5,545,140 A | 8/1996 | Conero et al. |
| 5,326,249 A | 7/1994 | Weissfloch et al. | 5,545,151 A | 8/1996 | O'Connor et al. |
| 5,328,460 A | 7/1994 | Lord et al. | 5,545,186 A | 8/1996 | Olson et al. |
| 5,330,511 A | 7/1994 | Boute et al. | 5,545,214 A | 8/1996 | Stevens |
| 5,337,750 A | 8/1994 | Walloch | 5,547,470 A | 8/1996 | Johnson et al. |
| 5,341,430 A | 8/1994 | Aulia et al. | 5,551,427 A | 9/1996 | Altman |
| 5,342,401 A | 8/1994 | Spano et al. | 5,551,439 A | 9/1996 | Hickey |
| 5,342,406 A | 8/1994 | Thompson | 5,554,185 A | 9/1996 | Block et al. |
| 5,344,388 A | 9/1994 | Maxwell et al. | 5,558,644 A | 9/1996 | Boyd et al. |
| 5,347,476 A | 9/1994 | McBean, Sr. | 5,564,434 A | 10/1996 | Halperin et al. |
| 5,348,210 A | 9/1994 | Linzell et al. | 5,575,770 A | 11/1996 | Melsky et al. |
| 5,348,536 A | 9/1994 | Young et al. | 5,584,803 A | 12/1996 | Stevens et al. |
| 5,350,413 A | 9/1994 | Miller et al. | 5,586,629 A | 12/1996 | Shoberg et al. |
| 5,352,180 A | 10/1994 | Candelon et al. | 5,593,430 A | 1/1997 | Renger |
| 5,353,622 A | 10/1994 | Theener | 5,594,665 A | 1/1997 | Walter et al. |
| 5,353,800 A | 10/1994 | Pohndorf et al. | 5,596,986 A | 1/1997 | Goldfarb |
| 5,354,200 A | 10/1994 | Klein et al. | 5,597,284 A | 1/1997 | Weltlich et al. |
| 5,354,316 A | 10/1994 | Keimel | 5,610,083 A | 3/1997 | Chan et al. |
| 5,354,319 A | 10/1994 | Wyborny et al. | 5,611,768 A | 3/1997 | Tutrone, Jr. |
| 5,360,407 A | 11/1994 | Leonard et al. | 5,612,497 A | 3/1997 | Walter et al. |
| 5,365,462 A | 11/1994 | McBean, Sr. | 5,615,671 A | 4/1997 | Schoonen et al. |
| 5,365,619 A | 11/1994 | Solomon | 5,619,991 A | 4/1997 | Sloane |
| 5,365,985 A | 11/1994 | Todd et al. | 5,625,946 A | 5/1997 | Wildeson et al. |
| 5,368,040 A | 11/1994 | Carney | 5,626,623 A | 5/1997 | Kieval et al. |
| 5,370,665 A | 12/1994 | Hudrlik | 5,626,630 A | 5/1997 | Markowitz et al. |
| 5,373,852 A | 12/1994 | Harrison et al. | 5,630,836 A | 5/1997 | Prem et al. |
| 5,375,073 A | 12/1994 | McBean | 5,634,255 A | 6/1997 | Bishop et al. |
| 5,377,128 A | 12/1994 | McBean | 5,637,083 A | 6/1997 | Bertrand et al. |
| 5,378,231 A | 1/1995 | Johnson et al. | 5,643,207 A | 7/1997 | Rise |
| 5,382,232 A | 1/1995 | Hague et al. | 5,645,116 A | 7/1997 | McDonald |
| 5,383,915 A | 1/1995 | Adams | 5,650,766 A | 7/1997 | Burgmann et al. |
| 5,388,578 A | 2/1995 | Yomtov et al. | 5,673,585 A | 10/1997 | Bishop et al. |
| 5,388,586 A | 2/1995 | Lee et al. | 5,676,690 A | 10/1997 | Noren et al. |
| 5,388,831 A | 2/1995 | Quadri et al. | 5,681,285 A | 10/1997 | Ford et al. |
| 5,394,909 A | 3/1995 | Mitchell et al. | 5,686,831 A | 11/1997 | Vandervalk et al. |
| 5,402,944 A | 4/1995 | Pape et al. | 5,687,734 A | 11/1997 | Dempsey et al. |
| 5,406,957 A | 4/1995 | Tansey | 5,693,076 A | 12/1997 | Kaemmerer |
| 5,409,009 A | 4/1995 | Olson | 5,702,368 A | 12/1997 | Stevens et al. |
| 5,411,031 A | 5/1995 | Yomtov | 5,702,427 A | 12/1997 | Ecker et al. |
| 5,411,551 A | 5/1995 | Winston et al. | 5,702,431 A | 12/1997 | Wang et al. |
| 5,411,552 A | 5/1995 | Andersen et al. | 5,704,352 A | 1/1998 | Tremblay et al. |
| 5,416,372 A | 5/1995 | Ljungstroem et al. | 5,715,786 A | 2/1998 | Seiberth et al. |
| 5,417,226 A | 5/1995 | Juma | 5,715,837 A | 2/1998 | Chen |
| 5,417,717 A | 5/1995 | Salo et al. | 5,720,436 A | 2/1998 | Buschor et al. |
| 5,425,362 A | 6/1995 | Siker et al. | 5,730,101 A | 3/1998 | Aupperle et al. |
| 5,431,171 A | 7/1995 | Harrison et al. | 5,732,710 A | 3/1998 | Rabinovich et al. |
| 5,431,694 A | 7/1995 | Snaper et al. | 5,733,313 A | 3/1998 | Barreras, Sr. et al. |
| 5,433,694 A | 7/1995 | Lim et al. | 5,738,652 A | 4/1998 | Boyd et al. |
| 5,437,605 A | 8/1995 | Helmy et al. | 5,742,233 A | 4/1998 | Hoffman et al. |
| 5,443,215 A | 8/1995 | Fackler | 5,743,267 A | 4/1998 | Nikolic et al. |
| 5,447,519 A | 9/1995 | Peterson | 5,749,369 A | 5/1998 | Rabinovich et al. |
| 5,449,368 A | 9/1995 | Kuzmak | 5,749,909 A | 5/1998 | Schroeppel et al. |
| 5,456,690 A | 10/1995 | Duong-Van | 5,755,687 A | 5/1998 | Donlon |
| 5,461,390 A | 10/1995 | Hoshen | 5,755,748 A | 5/1998 | Borza et al. |
| 5,464,435 A | 11/1995 | Neumann | 5,765,568 A | 6/1998 | Sweezer, Jr. et al. |
| 5,467,627 A | 11/1995 | Smith et al. | 5,769,812 A | 6/1998 | Stevens et al. |
| 5,474,226 A | 12/1995 | Joseph | 5,771,903 A | 6/1998 | Jakobsson |
| 5,479,818 A | 1/1996 | Walter et al. | 5,782,774 A | 7/1998 | Shmulewitz |
| 5,482,049 A | 1/1996 | Addiss et al. | 5,787,520 A | 8/1998 | Dunbar |
| 5,487,760 A | 1/1996 | Villafana | 5,791,344 A | 8/1998 | Schulman et al. |
| 5,493,738 A | 2/1996 | Sanderson et al. | 5,792,094 A | 8/1998 | Stevens et al. |
| 5,494,036 A | 2/1996 | Uber, III et al. | 5,792,179 A | 8/1998 | Sideris |
| 5,494,193 A | 2/1996 | Kirschner et al. | 5,795,325 A | 8/1998 | Valley et al. |
| 5,504,474 A | 4/1996 | Libman et al. | 5,796,827 A | 8/1998 | Coppersmith et al. |
| 5,505,916 A | 4/1996 | Berry, Jr. | 5,800,375 A | 9/1998 | Sweezer et al. |
| 5,507,412 A | 4/1996 | Ebert et al. | 5,807,265 A | 9/1998 | Itoigawa et al. |
| 5,507,737 A | 4/1996 | Palmskog et al. | 5,807,336 A | 9/1998 | Russo et al. |
| 5,507,785 A | 4/1996 | Deno | 5,810,015 A | 9/1998 | Flaherty |
| 5,509,888 A | 4/1996 | Miller | 5,810,757 A | 9/1998 | Sweezer, Jr. et al. |
| 5,509,891 A | 4/1996 | DeRidder | 5,814,016 A | 9/1998 | Valley et al. |

| Patent | Kind | Date | Inventor |
|---|---|---|---|
| 5,817,093 | A | 10/1998 | Williamson, IV et al. |
| 5,833,603 | A | 11/1998 | Kovacs et al. |
| 5,836,300 | A | 11/1998 | Mault |
| 5,836,886 | A | 11/1998 | Itoigawa et al. |
| 5,840,081 | A | 11/1998 | Andersen et al. |
| 5,849,225 | A | 12/1998 | Ebina et al. |
| 5,855,597 | A | 1/1999 | Jayaraman et al. |
| 5,855,601 | A | 1/1999 | Bessler et al. |
| 5,860,938 | A | 1/1999 | Lafontaine et al. |
| 5,861,018 | A | 1/1999 | Feierbach |
| 5,863,366 | A | 1/1999 | Snow |
| 5,868,702 | A | 2/1999 | Stevens et al. |
| 5,873,837 | A | 2/1999 | Lieber et al. |
| 5,875,953 | A | 3/1999 | Shioya et al. |
| 5,879,499 | A | 3/1999 | Corvi |
| 5,881,919 | A | 3/1999 | Womac et al. |
| 5,885,238 | A | 3/1999 | Stevens et al. |
| 5,887,475 | A | 3/1999 | Muldner |
| 5,899,927 | A | 5/1999 | Ecker et al. |
| 5,916,179 | A | 6/1999 | Sharrock |
| 5,916,237 | A | 6/1999 | Schu |
| 5,935,078 | A | 8/1999 | Feierbach |
| 5,938,669 | A | 8/1999 | Klaiber et al. |
| 5,951,487 | A | 9/1999 | Brehmeier-Flick et al. |
| 5,957,861 | A | 9/1999 | Combs et al. |
| 5,967,986 | A | 10/1999 | Cimochowski et al. |
| 5,971,934 | A | 10/1999 | Scherer et al. |
| 5,974,873 | A | 11/1999 | Nelson et al. |
| 5,978,985 | A | 11/1999 | Thurman |
| 5,995,874 | A | 11/1999 | Borza et al. |
| 6,007,516 | A * | 12/1999 | Burbank et al. ......... 604/288.03 |
| 6,015,386 | A | 1/2000 | Kensey et al. |
| 6,015,387 | A | 1/2000 | Schwartz et al. |
| 6,019,729 | A | 2/2000 | Itoigawa et al. |
| 6,024,704 | A | 2/2000 | Meador et al. |
| 6,030,413 | A | 2/2000 | Lazarus |
| 6,035,461 | A | 3/2000 | Nguyen |
| 6,053,873 | A | 4/2000 | Govari et al. |
| 6,056,723 | A | 5/2000 | Donlon |
| 6,058,330 | A | 5/2000 | Borza et al. |
| 6,059,757 | A | 5/2000 | Macoviak et al. |
| 6,067,474 | A | 5/2000 | Schulman et al. |
| 6,067,991 | A | 5/2000 | Forsell et al. |
| 6,076,016 | A | 6/2000 | Feierbach |
| 6,083,174 | A | 7/2000 | Brehmeier-Flick et al. |
| 6,090,096 | A | 7/2000 | St. Goar et al. |
| 6,102,678 | A | 8/2000 | Peclat et al. |
| 6,102,856 | A | 8/2000 | Groff et al. |
| 6,102,922 | A | 8/2000 | Jakobsson et al. |
| 6,106,477 | A | 8/2000 | Miesel et al. |
| 6,106,551 | A | 8/2000 | Crossett et al. |
| 6,110,145 | A | 8/2000 | Macoviak |
| 6,113,553 | A | 9/2000 | Chubbuck |
| 6,131,664 | A | 10/2000 | Sonnier |
| 6,135,945 | A | 10/2000 | Sultan |
| 6,159,156 | A | 12/2000 | Van Bockel et al. |
| 6,162,180 | A | 12/2000 | Miesel et al. |
| 6,162,245 | A | 12/2000 | Jayaraman et al. |
| 6,168,614 | B1 | 1/2001 | Andersen et al. |
| 6,234,745 | B1 | 5/2001 | Pugh et al. |
| 6,240,316 | B1 | 5/2001 | Richmond et al. |
| 6,240,318 | B1 | 5/2001 | Phillips |
| 6,245,102 | B1 | 6/2001 | Jayaraman |
| 6,248,080 | B1 | 6/2001 | Miesel et al. |
| 6,251,093 | B1 | 6/2001 | Valley et al. |
| 6,269,819 | B1 | 8/2001 | Oz et al. |
| 6,277,078 | B1 | 8/2001 | Porat et al. |
| 6,292,697 | B1 | 9/2001 | Roberts |
| 6,309,350 | B1 | 10/2001 | VanTassel et al. |
| 6,315,769 | B1 | 11/2001 | Peer et al. |
| 6,319,208 | B1 | 11/2001 | Abita et al. |
| 6,328,699 | B1 | 12/2001 | Eigler et al. |
| 6,338,735 | B1 | 1/2002 | Stevens |
| 6,357,438 | B1 | 3/2002 | Hansen |
| 6,360,122 | B1 | 3/2002 | Fischell et al. |
| 6,360,822 | B1 | 3/2002 | Robertson et al. |
| 6,366,817 | B1 | 4/2002 | Kung |
| 6,379,308 | B1 | 4/2002 | Brockway et al. |
| 6,379,380 | B1 | 4/2002 | Satz |
| 6,398,752 | B1 | 6/2002 | Sweezer, Jr. et al. |
| 6,409,674 | B1 | 6/2002 | Brockway et al. |
| 6,423,031 | B1 | 7/2002 | Donlon |
| 6,430,444 | B1 | 8/2002 | Borza et al. |
| 6,431,175 | B1 | 8/2002 | Penner et al. |
| 6,432,040 | B1 | 8/2002 | Meah |
| 6,443,887 | B1 | 9/2002 | Derus et al. |
| 6,443,893 | B1 | 9/2002 | Schnakenberg et al. |
| 6,450,173 | B1 | 9/2002 | Forsell et al. |
| 6,450,946 | B1 | 9/2002 | Forsell et al. |
| 6,453,907 | B1 | 9/2002 | Forsell et al. |
| 6,454,698 | B1 | 9/2002 | Forsell et al. |
| 6,454,699 | B1 | 9/2002 | Forsell et al. |
| 6,454,700 | B1 | 9/2002 | Forsell et al. |
| 6,454,701 | B1 | 9/2002 | Forsell et al. |
| 6,461,292 | B1 | 10/2002 | Forsell et al. |
| 6,461,293 | B1 | 10/2002 | Forsell et al. |
| 6,463,329 | B1 | 10/2002 | Goedeke |
| 6,463,935 | B1 | 10/2002 | Forsell et al. |
| 6,464,628 | B1 | 10/2002 | Forsell et al. |
| 6,470,212 | B1 | 10/2002 | Weijand et al. |
| 6,470,892 | B1 | 10/2002 | Forsell et al. |
| 6,471,635 | B1 | 10/2002 | Forsell et al. |
| 6,475,136 | B1 | 11/2002 | Forsell et al. |
| 6,475,170 | B1 | 11/2002 | Doron et al. |
| 6,482,145 | B1 | 11/2002 | Forsell et al. |
| 6,482,171 | B1 | 11/2002 | Corvi et al. |
| 6,482,177 | B1 | 11/2002 | Leinders et al. |
| 6,486,588 | B2 | 11/2002 | Doron et al. |
| 6,503,189 | B1 | 1/2003 | Forsell et al. |
| 6,504,286 | B1 | 1/2003 | Porat et al. |
| 6,531,739 | B2 | 3/2003 | Cable et al. |
| 6,533,719 | B2 | 3/2003 | Kuyava et al. |
| 6,533,733 | B1 | 3/2003 | Hylton et al. |
| 6,542,350 | B1 | 4/2003 | Rogers |
| 6,558,321 | B1 | 5/2003 | Burd et al. |
| 6,558,994 | B2 | 5/2003 | Cha et al. |
| 6,573,563 | B2 | 6/2003 | Lee et al. |
| 6,582,462 | B1 | 6/2003 | Andersen et al. |
| 6,599,250 | B2 | 7/2003 | Webb et al. |
| 6,605,112 | B1 | 8/2003 | Moll et al. |
| 6,629,534 | B1 | 10/2003 | ST. Goar et al. |
| 6,640,137 | B2 | 10/2003 | MacDonald |
| 6,641,610 | B2 | 11/2003 | Wolf et al. |
| 6,645,143 | B2 | 11/2003 | VanTassel et al. |
| 6,673,109 | B2 | 1/2004 | Cox |
| 6,678,561 | B2 | 1/2004 | Forsell et al. |
| 6,682,480 | B1 | 1/2004 | Habib et al. |
| 6,682,503 | B1 | 1/2004 | Fariss et al. |
| 6,682,559 | B2 | 1/2004 | Myers et al. |
| 6,695,866 | B1 | 2/2004 | Kuehn et al. |
| 6,709,385 | B2 | 3/2004 | Forsell et al. |
| 6,718,200 | B2 | 4/2004 | Marmaropoulos et al. |
| 6,719,787 | B2 | 4/2004 | Cox |
| 6,719,788 | B2 | 4/2004 | Cox |
| 6,719,789 | B2 | 4/2004 | Cox |
| 6,731,976 | B2 | 5/2004 | Penn et al. |
| 6,733,525 | B2 | 5/2004 | Yang et al. |
| 6,736,846 | B2 | 5/2004 | Cox |
| 6,752,813 | B2 | 6/2004 | Goldfarb et al. |
| 6,796,942 | B1 | 9/2004 | Kreiner et al. |
| 6,822,343 | B2 | 11/2004 | Estevez |
| 6,851,628 | B1 | 2/2005 | Garrison et al. |
| 6,855,115 | B2 | 2/2005 | Fonseca et al. |
| 6,889,772 | B2 | 5/2005 | Buytaert et al. |
| 6,890,300 | B2 | 5/2005 | Lloyd et al. |
| 6,896,651 | B2 | 5/2005 | Gross et al. |
| 6,896,690 | B1 | 5/2005 | Lambrecht et al. |
| 6,913,600 | B2 | 7/2005 | Valley et al. |
| 6,915,165 | B2 | 7/2005 | Forsell et al. |
| 6,926,246 | B2 | 8/2005 | Ginggen et al. |
| 6,929,653 | B2 | 8/2005 | Strecter |
| 6,932,792 | B1 | 8/2005 | St. Goar et al. |
| 6,951,229 | B2 | 10/2005 | Garrison et al. |
| 6,951,571 | B1 | 10/2005 | Srivastava |
| 6,953,429 | B2 | 10/2005 | Forsell et al. |
| 6,961,619 | B2 | 11/2005 | Casey |
| 6,970,742 | B2 | 11/2005 | Mann et al. |
| 6,979,350 | B2 | 12/2005 | Moll et al. |

| | | |
|---|---|---|
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,118,526 B2 * | 10/2006 | Egle .............................. 600/37 |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0131383 A1 * | 6/2005 | Chen et al. .................... 604/502 |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 * | 9/2006 | Hassler et al. .................. 600/37 |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |

| | | |
|---|---|---|
| CN | 1059035 | 2/1992 |
| CN | 1119469 | 3/1996 |
| CN | 1241003 | 1/2000 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0033738 | 6/2000 |
| WO | WO-0072899 | 12/2000 |
| WO | WO-014487 | 1/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

* cited by examiner

FIG. 1A <u>PRIOR ART</u>
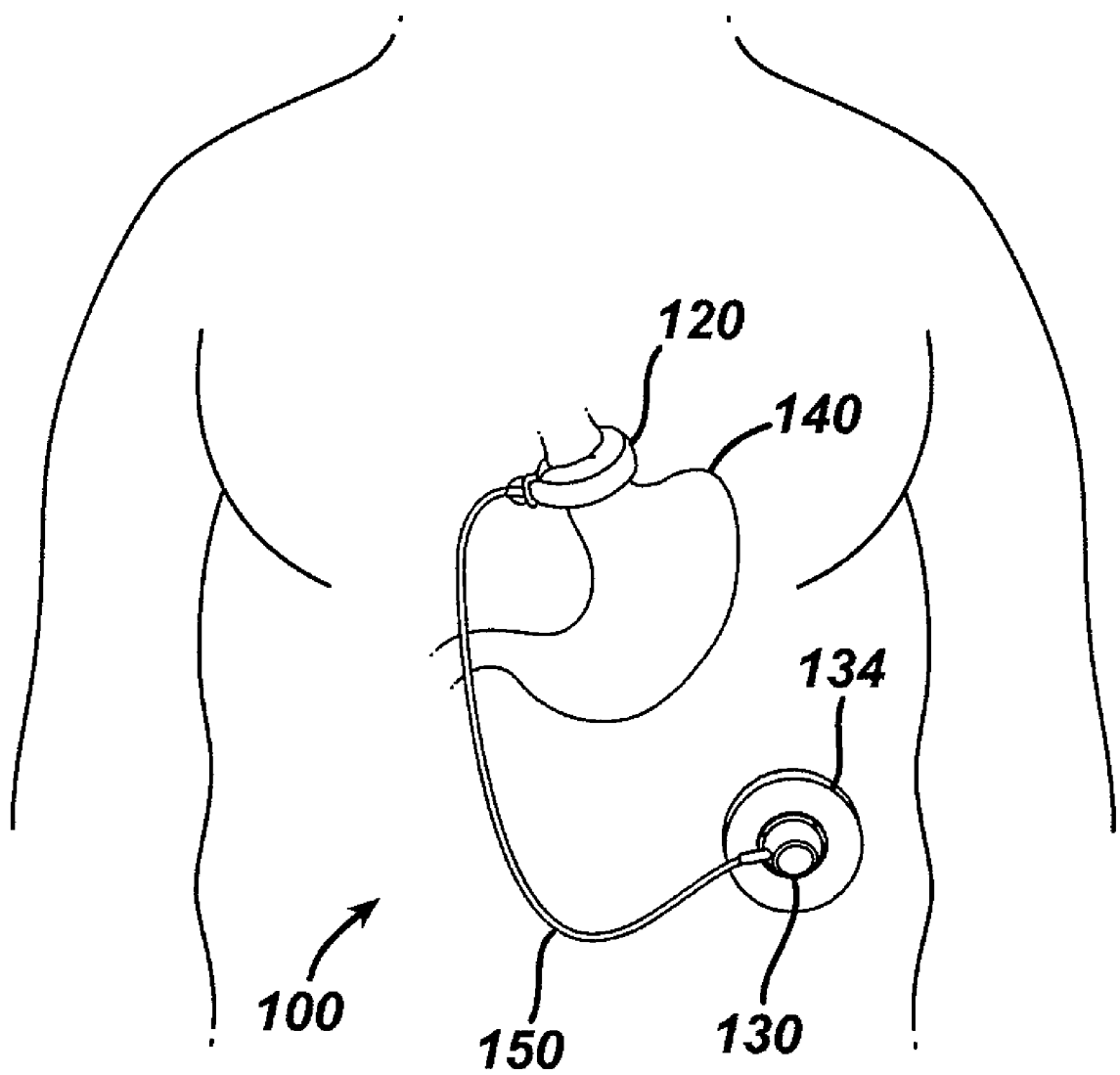

METHODS FOR IMPLANTING A GASTRIC RESTRICTION DEVICE

FIELD OF THE INVENTION

The present invention relates to surgical methods, and in particular to methods for implanting a restriction device.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With the advent of various restriction devices, there is a need for improved methods for implanting such devices. Accordingly, novel methods are provided for implanting a gastric restriction device.

SUMMARY OF THE INVENTION

Various exemplary methods are provided for implanting a restriction device. In one embodiment, a method for implanting a restriction system is provided and includes forming a pathway through a skin incision, coupling a catheter exiting through the skin incision to a housing such that the housing is coupled, via the catheter, to a restriction device implanted to form a restriction, forming a tunnel extending from the pathway, and positioning the housing within the tunnel. In an exemplary embodiment, the tunnel extends transverse to a longitudinal axis of the pathway, and the pathway extends from a skin incision and into a body cavity. The method can also include advancing the restriction device through the pathway and into the body cavity.

The tunnel can be formed using various techniques. For example, the tunnel can be a finger tunnel. In other embodiments, an elongate member can be inserted into the pathway and manipulated to form a tunnel extending from the pathway. The location of the tunnel can also vary, but in an exemplary embodiment the tunnel is formed adjacent to a fascia layer.

The housing can have various configurations, and in one embodiment the device can include a first housing that is coupled to a second housing. The method can further include positioning the second housing adjacent to the pathway. The restriction device can also include a sensor that measures at least one physiological parameter. In one embodiment, the sensor can be a pressure sensor. The sensor can be disposed anywhere within the system, including within one or more of the housings. Depending on the particular configuration of the device, in other embodiments the housing can be in fluid communication with the restriction device.

In another embodiment, the pathway can be a primary pathway and the tunnel can extend from the primary pathway to a secondary pathway. The method can include advancing the catheter from one of the primary pathway and the secondary pathway, through the tunnel, to the other one of the primary pathway and the secondary pathway. The catheter can be coupled to the housing prior to or after advancing the catheter. In another embodiment, positioning the housing within the tunnel can include retracting the catheter into the tunnel to pull the housing through one of the primary pathway and the secondary pathway and into the tunnel.

In another embodiment, a method for implanting a restriction system is provided and includes advancing a restriction device through a pathway extending from a skin incision into a body cavity. A catheter coupled to the restriction device can optionally extend through the pathway and exit the skin incision, or it can be fully disposed within the body cavity. The method can also include forming a single connection between a catheter coupled to the restriction device and one of a first housing and a second housing. The first and second housings can be coupled to one another by a connector extending therebetween. The method can also include implanting the first and second housings in tissue.

In one embodiment, the first housing can be implanted in a tunnel extending from the pathway and adjacent to a fascia layer, and the second housing can be implanted in the pathway at an offset location. In another embodiment, the pathway can be a first pathway, and the tunnel can extend from the first pathway to a second pathway. Implanting the first and second housings can include retracting the catheter into the tunnel. In an exemplary embodiment, the catheter is advanced from the first pathway to the second pathway prior to forming a single connection between the catheter and one of the first and second housings.

In other aspects, a method of implanting a restriction system is provided and includes advancing a restriction device through a primary pathway extending from a skin incision to a body cavity to position the restriction device around an organ to be restricted, forming a tunnel between the primary pathway and a secondary pathway, advancing the trailing end of a catheter coupled to the restriction device through the tunnel, coupling the trailing end of the catheter to a housing, and implanting the housing in tissue. In one embodiment, the trailing end of the catheter can exit from the skin incision when the restriction device is advanced through the primary pathway.

In an exemplary embodiment, advancing the trailing end of the catheter through the tunnel can include advancing the trailing end of the catheter through the primary pathway, across the tunnel, and through the secondary pathway such that the trailing end of the catheter exits the secondary pathway. Implanting the housing can include retracting the catheter to position the housing within the tunnel, and implanting the housing in the tunnel. The catheter can be retracted by, for example, pulling on a portion of the catheter extending from the primary pathway. In an exemplary embodiment, the housing is a sensor housing that is coupled to a fill port, and the method can include implanting the fill port in tissue.

BRIEF DESCRIPTION OF THE DRAWINGS

The invention will be more fully understood from the following detailed description taken in conjunction with the accompanying drawings, in which:

FIG. 1A is a front view illustration of a prior art gastric restriction device implanted in a patient to form a restriction in the patient's stomach;

DETAILED DESCRIPTION OF THE INVENTION

Figure 1B:
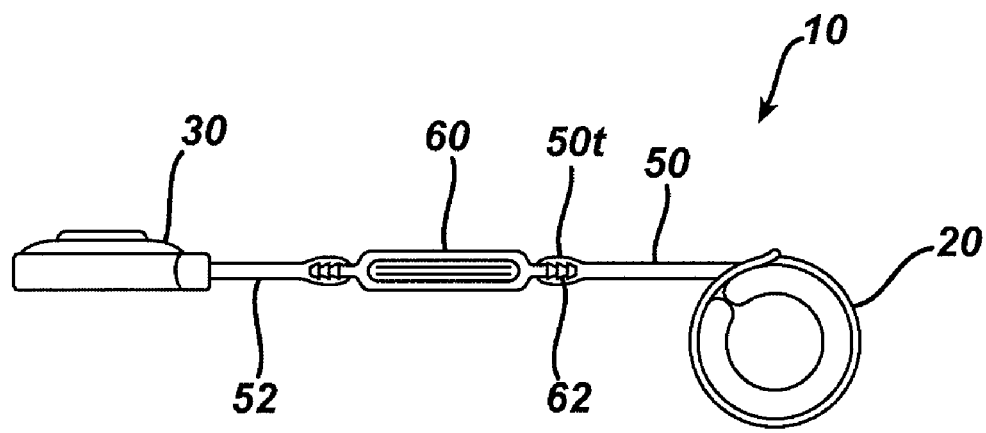
FIG. 1B is a side view of another embodiment of a prior art gastric restriction device having an injection port coupled to a sensor housing in an in-line configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally discloses various exemplary methods for implanting a restriction device for forming a restriction in a patient. The methods can be used with a variety of restriction devices, but in an exemplary embodiment the methods are used for implanting a gastric restriction device. While various types of gastric restriction devices are known, including electrical, mechanical, and/or fluid-based devices, for reference purposes the methods disclosed herein are discussed in connection various embodiments of a gastric restriction device disclosed in commonly-owned U.S. Publication No. 2006/0211913 of Dlugos et al. (hereinafter "Dlugos") filed on Mar. 7, 2006 and entitled "Non-Invasive Pressure Measurement In A fluid Adjustable Restrictive Device," which is hereby incorporated by reference in its entirety. A person skilled in the art will appreciate that the method is not intended to be limited to use with any particular device.

FIG. 1A illustrates one embodiment of an implantable restriction device, as disclosed in Dlugos. As shown, the implantable restriction device 100 generally includes an adjustable gastric band 120 that is configured to be positioned around the upper portion of a patient's stomach 140, and an injection port 130 that is fluidly coupled to the adjustable gastric band 120, e.g., via a catheter 150. A person skilled in the art will appreciate that the catheter can be a single, unitary member, or it can be formed from multiple components joined together. The injection port 130 is adapted to allow fluid to be introduced into and removed from the gastric band 20 to thereby adjust the size of the band 120, and thus the pressure applied to the stomach. The injection port 130 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient.

Figure 1C:
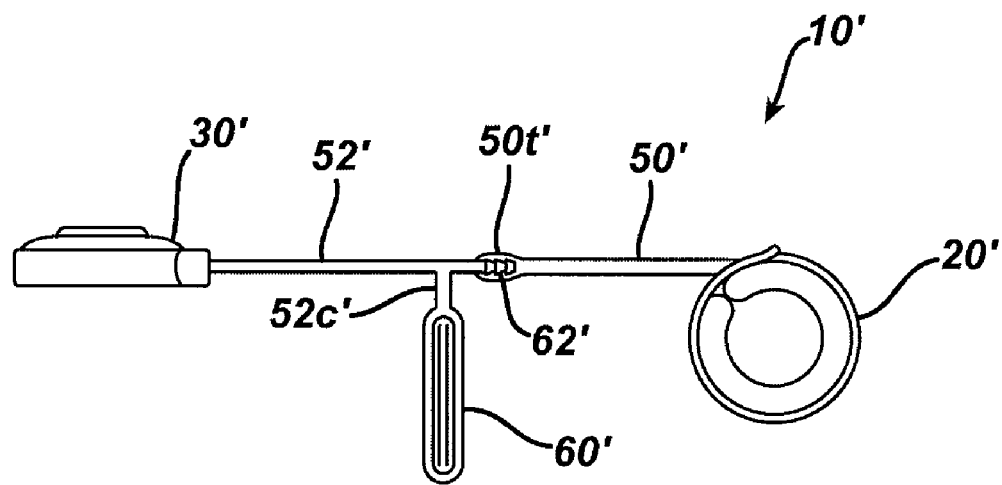
FIG. 1C is a side view of another embodiment of a prior art gastric restriction device having an injection port coupled to a sensor housing in a T-configuration.

The illustrated device 100 also includes a pressure reading device 134 for reading the pressure of the fluid within the closed fluid circuit of the device 100. While Dlugos discloses a pressure reading device 134, the device could be any sensing device for sensing various parameters. The sensing device can also have various configurations and it can be coupled to or positioned anywhere in the gastric restriction device 100. In the illustrated embodiment, the pressure reading device 134 is coupled to the injection port 130. In another embodiment, as shown in FIG. 1B, Dlugos discloses a device 10 having a separate sensor housing 60 that is disposed in-line with the gastric band 20 and the injection port 30. In particular, a first catheter portion 50$a$ is coupled between the sensor housing 60 and the gastric band 20 and a second catheter portion 50$b$ is coupled between the injection port 30 and the sensor housing 60. In another embodiment, the gastric restriction device can have a Y-configuration or T-shaped configuration. As shown in FIG. 1C, Dlugos discloses a device 10' having include a catheter 52' with a T-shaped intersection 52$c$' with terminal ends that mate to the injection port 30' and the sensor housing 60'. While not disclosed by Dlugos, the third terminal end can mate, e.g., via connector 62', to the terminal end 50$t$' of the catheter 50' extending from the gastric band 20'. A person skilled in the art will appreciate that the gastric restriction device can have a variety of other configurations, and the sensor, if provided, can be implanted anywhere within the system, including within the injection port. Moreover, the system also may not have an injection port, but instead may have a single housing containing a sensor or contain other apparatus. Various configurations are possible, and any known restriction system or device can be used with the methods of the present invention.

Figure 2:
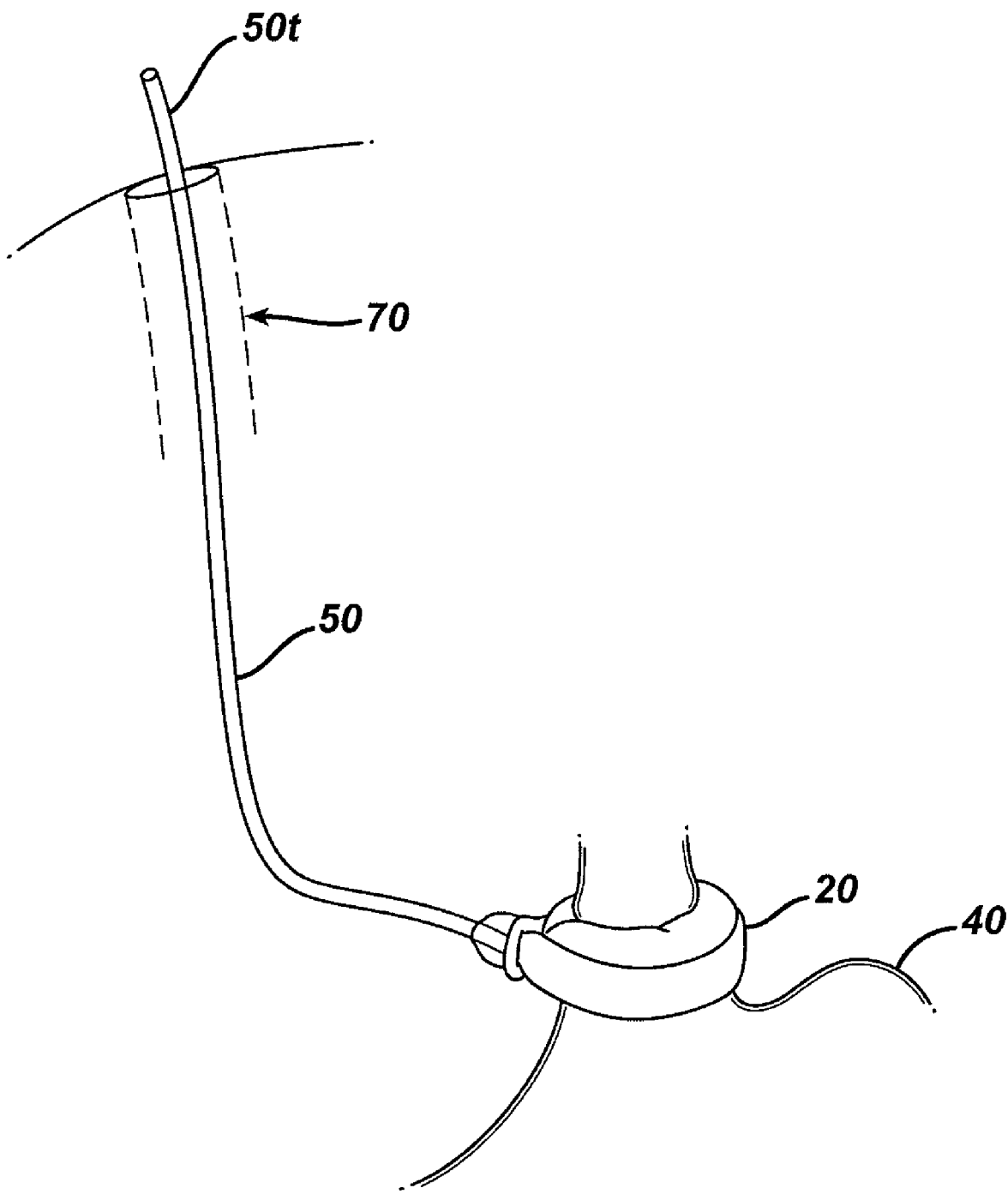
FIG. 2 is a side view illustration showing a first pathway extending from a skin incision to a body cavity containing a gastric band implanted to form a restriction in a stomach, showing a catheter coupled to the gastric band exiting from the first pathway.

In order to implant a restriction device, such as the gastric devices disclosed by Dlugos, a first pathway is typically formed through the stomach wall to provide access to the abdominal cavity. This can be achieved using various techniques known in the art, but in one exemplary embodiment a small skin incision is formed and a trocar is inserted through the skin incision until the tip of the trocar penetrates into the abdominal cavity. The trocar will thus form a primary or first pathway into the abdomen. This pathway can be used to introduce a gastric band. While only one pathway is shown, additional pathways are often created to provide access for various other devices, such as an endoscope for viewing the surgical site. Various techniques are known in the art for implanting a gastric band to form a restriction around the upper portion of a patient's stomach. By way of non-limiting example, U.S. Pat. No. 6,102,922 filed on Jun. 29, 1998 and entitled "Surgical Method and Device for Reducing Food Intake of a Patient," and U.S. Pat. No. 4,592,339 filed on Jun. 12, 1985 and entitled "Gastric Banding Device," which are hereby incorporated by reference in their entireties, disclose various methods for implanting a gastric band. FIG. 2 illustrates a first pathway 70 extending through a skin surface and into an abdominal cavity, showing the gastric restriction device 10 of FIG. 1B having the gastric band 20 positioned to form a restriction around an upper portion of a stomach 40, and showing the catheter 50 extending from the gastric band 20 and through the pathway such that the terminal end 50$t$ of the catheter 50 exits the skin incision and remains external to the patient's body. While not shown, in other embodiments the catheter 50, including the terminal end 50$t$, can be fully disposed within the body cavity.

Once the gastric band 20 is implanted, the terminal end 50$t$ of the catheter 50 can be connected to one or more housings and the housing(s) can be implanted in tissue. In an exemplary embodiment, only a single connection needs to be made between the terminal end 50$t$ of the catheter 50 and the housing(s). For example, where the restriction device 10 includes two or more housings, the housings can be pre-connected to one another during manufacturing and packaged together as a single sterile package. The terminal end 50$t$ of the catheter 50 extending from the gastric band 20 can thus be connected to a connector. Thus, with the device 10 of FIG. 1B, for example, the sensor housing 60 and injection port 30 can be pre-connected to one another during manufacturing, and the terminal end 50$t$ of the catheter can be connected to a connector 62 formed on the sensor housing 60 during the surgical procedure. Similarly, with the device 10' of FIG. 1C, the sensor housing 60' and injection port 30' can be pre-connected to one another during manufacturing and package together as a single sterile package. The terminal end 50$t$' of the catheter 50' extending from the gastric band 20' can be connected to a connector 62' formed on the catheter 52' that couples the sensor housing 60' and the injection port 30'. As previously noted, while the two housings are referred to as a "sensor housing" and an "injection port," the housings can contain various components for performing various functions, and the device can include any number of housings.

With the terminal end of the catheter connected to one or more housings, the housings can be implanted in tissue. The particular implant location can vary depending on the configuration of the device. For example, where the device includes an injection port, the port is preferably implanted just beneath the tissue surface to allow a needle or other device to be penetrated through tissue and into the injection port to add or remove fluid from the gastric restriction device. Where the device includes a sensor housing, the sensor housing is also preferably implanted in tissue at a location that is accessible to allow for wireless communication with the sensor, thus allowing data and/or energy to be transmitted between an external device and the sensor. In certain exemplary embodiments, the port and/or sensor housing are implanted on the fascia layer beneath up to 10 cm to 15 cm of subcutaneous abdominal fat.

The particular method for implanting the housing(s) can vary depending on the configuration of the device. FIGS. 3A-5 illustrate one exemplary embodiment of a method for implanting a restriction device having a T- or Y-configuration, such as the restriction device 10' of FIG. 1C. FIGS. 6-12B illustrate another exemplary embodiment of a method for implanting a device having at least one housing that is in-line with the gastric band, such as the device 10 of FIG. 1A. Again, a person skilled in the art will appreciate that the particular configuration can vary, and that the various methods disclosed herein can be used with any restriction device. Moreover, the various steps can be performed in any order.

Figure 3A:
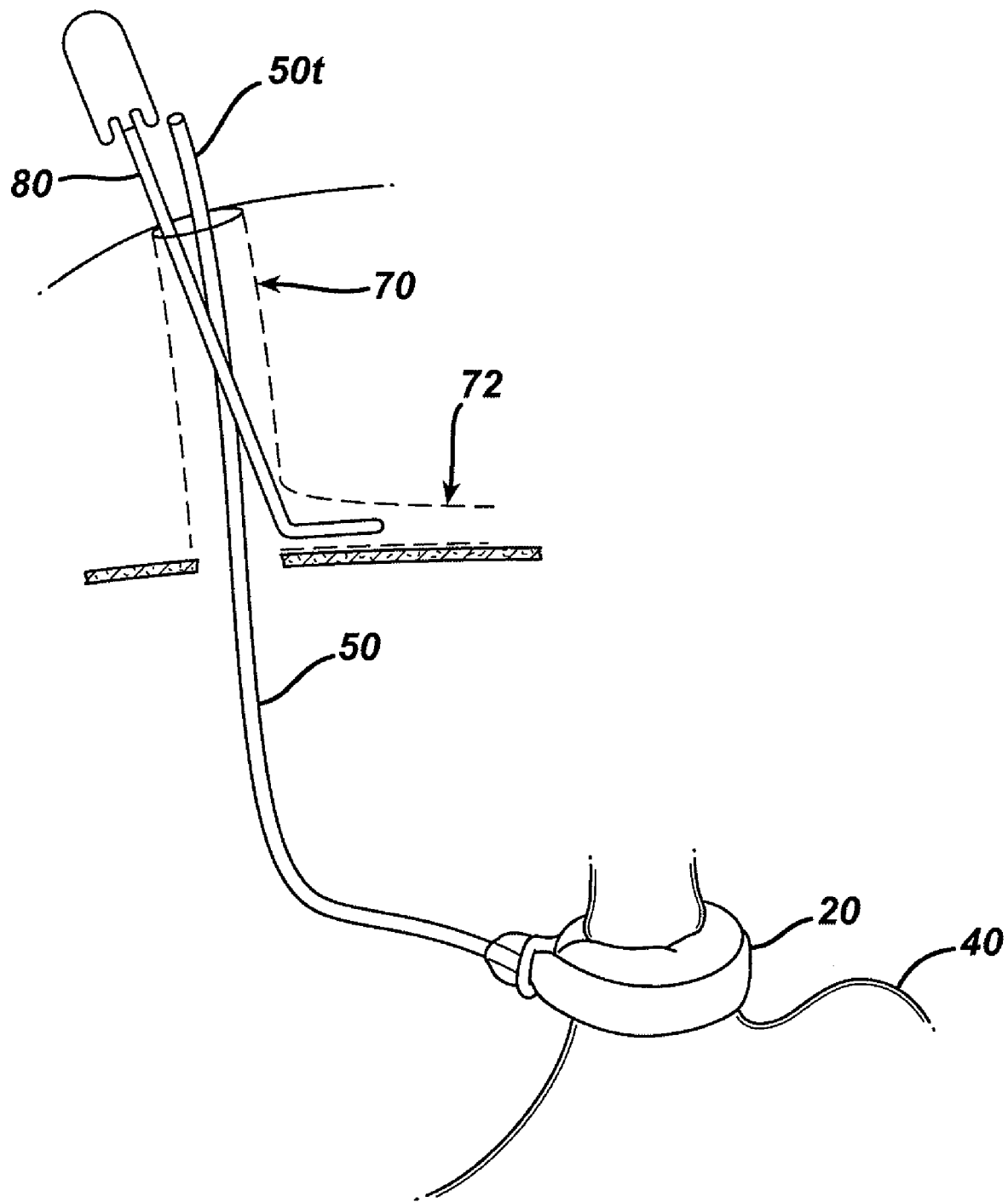
FIG. 3A is a side view illustration showing an elongate device being used to form a tunnel extending from the first pathway of FIG. 2.
Figure 3B:
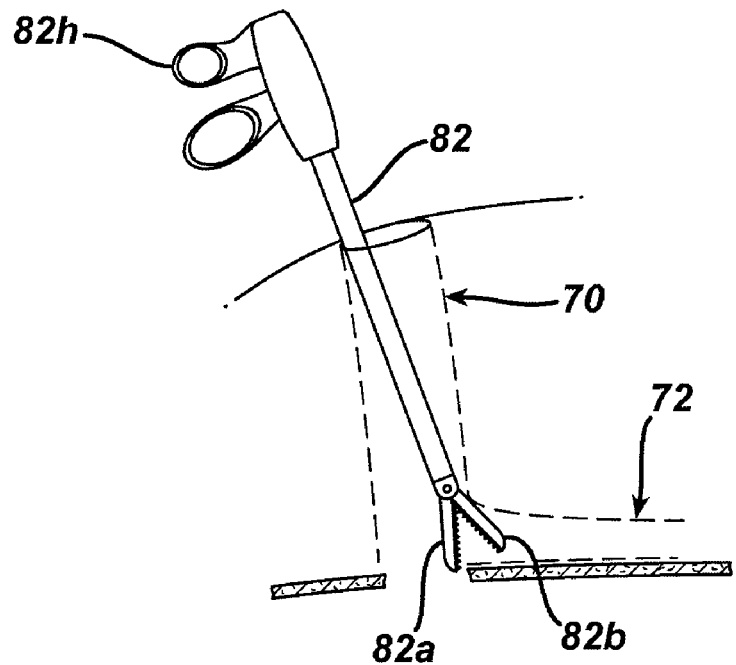
FIG. 3B is a side view illustration showing graspers being used to form a tunnel extending from the first pathway of FIG. 2.
Figure 3C:
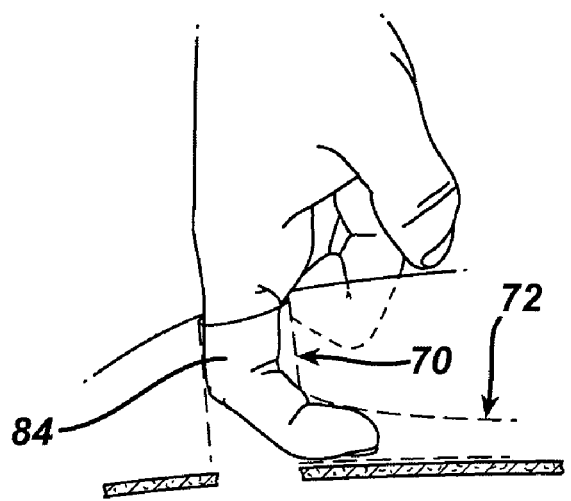
FIG. 3C is a side view illustration showing a finger being used to form a tunnel extending from the first pathway of FIG. 2.

As shown in FIGS. 3A-3C, in an exemplary embodiment at least one tunnel 72 is formed extending from the first pathway 70. The particular direction and orientation of the tunnel 72 can vary, however as shown the tunnel 72 extends laterally outward from the first pathway 70 in a direction transverse to a longitudinal axis of the first pathway 70. As a result, the tunnel 72 extends across the fascia layer, thus allowing at least one housing to be implanted and/or anchored to the fascia. A person skilled in the art will appreciate that the tunnel 72 can be formed at any particular point in time during the procedure, including prior to or after connecting the terminal end of the catheter to the housing(s). Moreover, where a trocar or other device is used to gain access to the abdominal cavity, the trocar or other device can remain within the first pathway 70 or it can be removed during tunnel formation. Several additional tunnels can also be formed, and the particular quantity can vary depending on the configuration of the device.

Various techniques can be used to form the tunnel 72. In one embodiment, as shown in FIG. 3A, the tunnel is formed using a device having an elongate shaft with a flexible and/or bent distal end, such as the Goldfinger™ device 80 available from Ethicon Endo-Surgery and used as a surgical dissector and suture retrieval device. U.S. Publication No. 2007/0185519 of Hassler et al. filed on Feb. 7, 2006 and entitled "Articulating Surgical Instrument," which is hereby incorporated by reference in its entirety, discloses one exemplary embodiment of such a device. The device 80 can be inserted through the pathway 70 and manipulated to separate the tissue and form a tunnel 72 extending transverse or laterally from the first pathway 70. The length or depth of the tunnel can vary, but preferably the tunnel has a size sufficient to receive at least a portion of a housing therein. The size can thus vary depending on the particular configuration of the housing.

In another embodiment, as shown in FIG. 3B, the tunnel 72 can be formed using a tissue-grasping and/or cutting device. FIG. 3B illustrates graspers 82 having opposed jaws 82a, 82b formed on the distal end thereof and configured to grasp tissue. The device 82 can be inserted through the first pathway 70, and a handle 82h on the device 82 can be manipulated to open and close the jaws 82a, 82b, thus allowing the jaws 82a, 82b to grasp and move and/or remove tissue to form the tunnel 72.

In yet another embodiment, as shown in FIG. 3C, the tunnel 72 can be formed using one's finger. In particular, the surgeon or other surgical staff can insert their finger 84 into the first pathway 70 and manipulate the finger to form the tunnel 72. A person skilled in the art will appreciate that a variety of other tools and techniques can be used to form a tunnel 72 extending from the first pathway 70. For example, in other embodiments the tunnel 72 can be formed internally from devices disposed within the body cavity.

Figure 4:
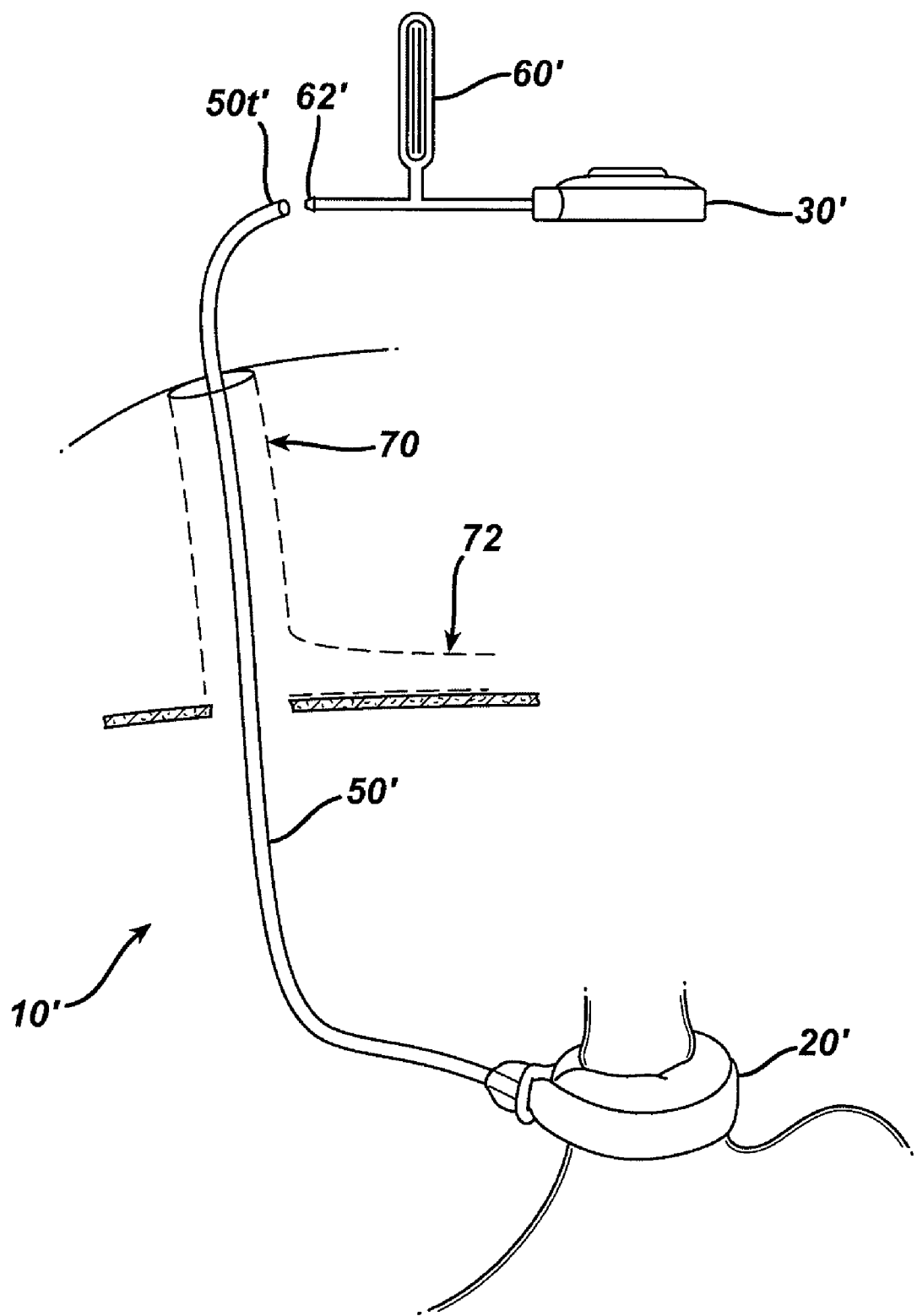
FIG. 4 is a side view illustration showing the sensor housing and injection port of FIG. 1C being coupled to a catheter exiting from the first pathway.
Figure 5:
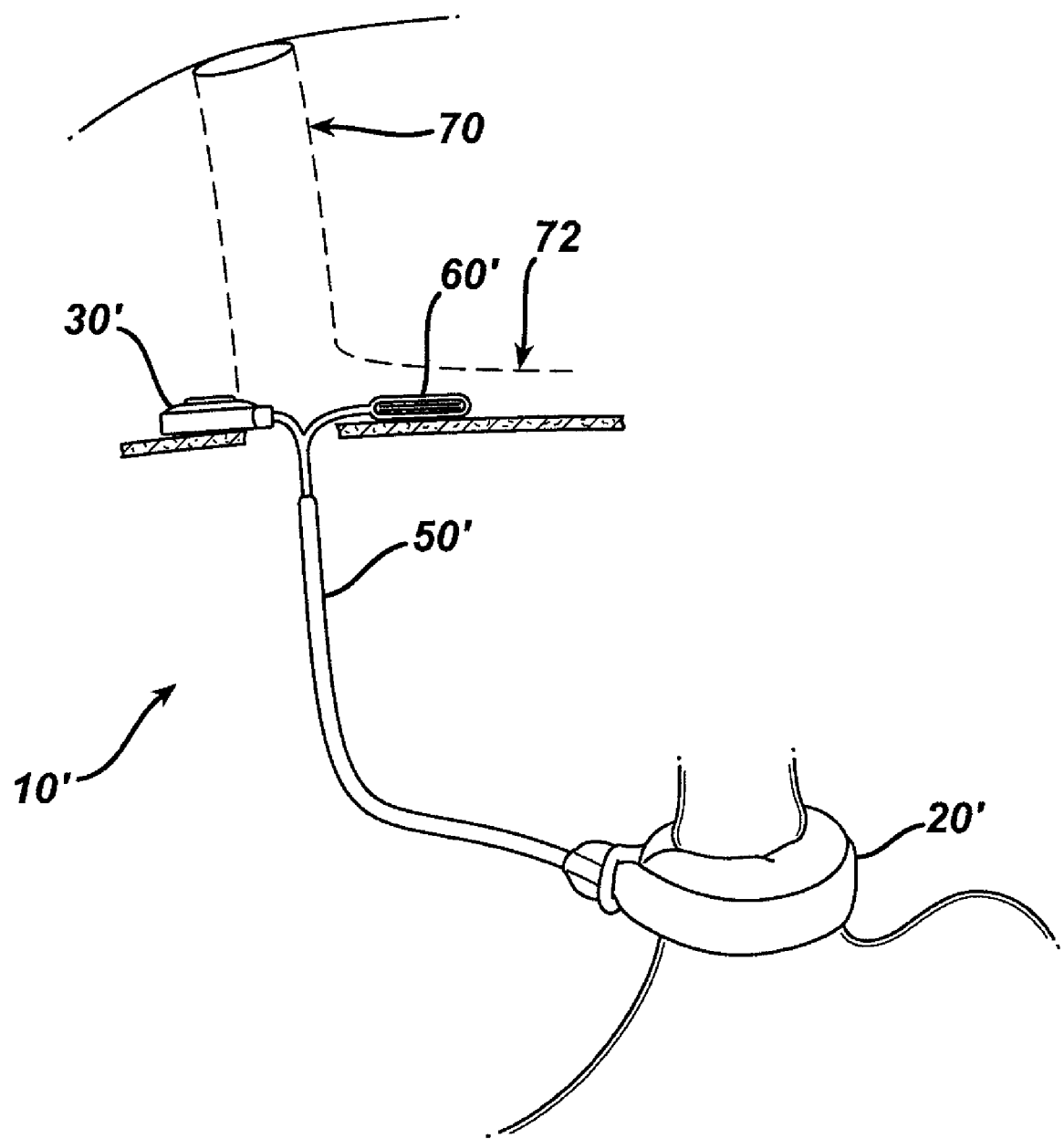
FIG. 5 is a side view illustration showing the sensor housing and injection port of FIG. 4 implanted within the tunnel and first pathway.
Figure 6:
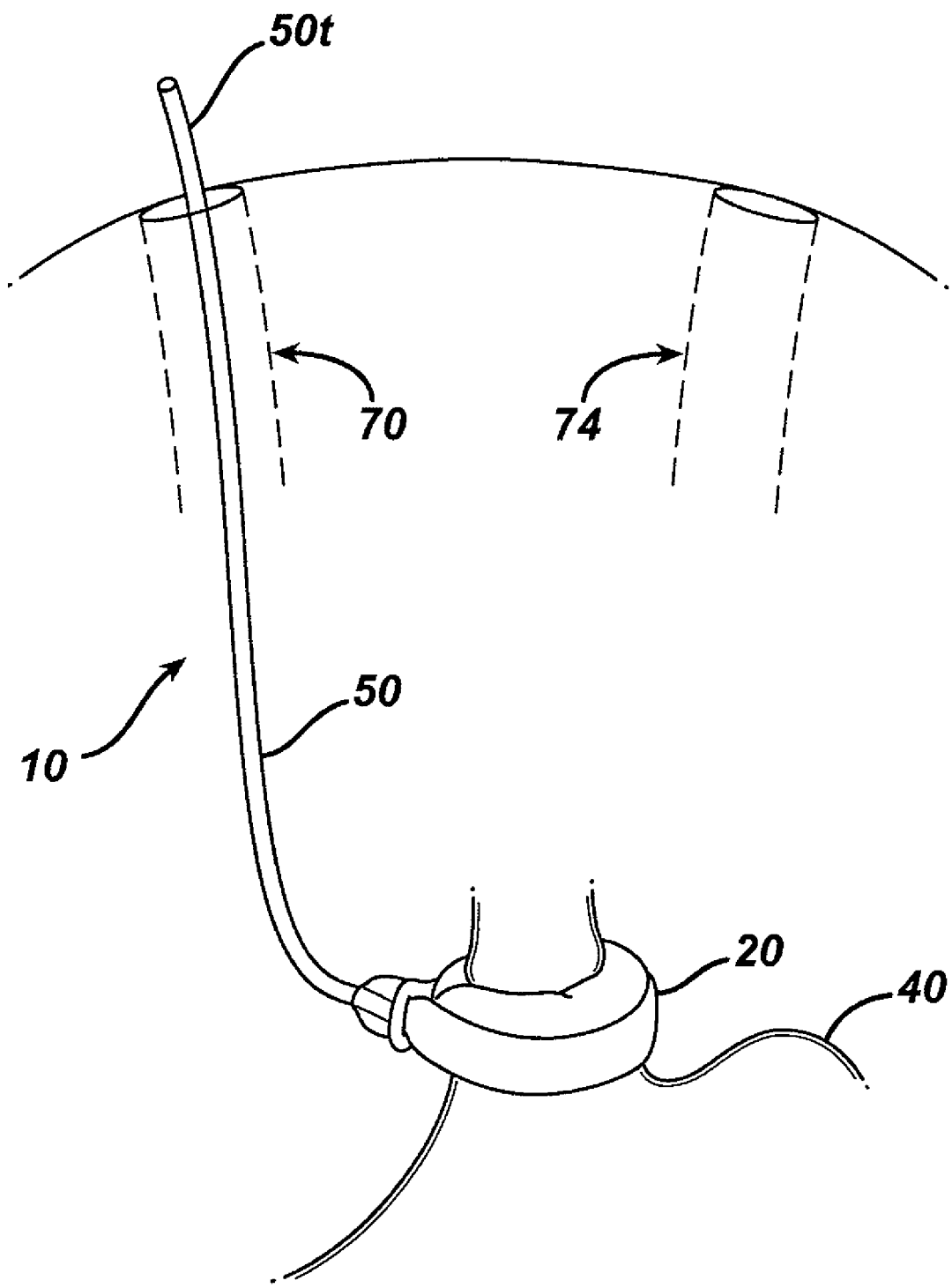
FIG. 6 is a side view illustration showing a second pathway being formed at a distance apart from a first pathway having a catheter extending therefrom and coupled to a gastric band.

Once the tunnel 72 is formed, one or more housings coupled to the gastric restriction device can be implanted in the tunnel 72. FIG. 4 illustrates the connector 62' on device 10' of FIG. 1C about to be connected to the terminal end 50t' of the catheter 50', and FIG. 5 illustrates the sensor housing 60' and the injection port 30' implanted. The housings can be implanted by inserting the sensor housing 60', either manually or using an insertion tool, through the pathway 70 and into the tunnel 72. In an exemplary embodiment, the sensor housing 60' is fully disposed within the tunnel 72 and is positioned to rest on the fascia. The sensor housing 60' can optionally be anchored to the fascia using, for example, sutures or other tissue engaging mechanisms, or it can merely rest on the fascia within the tunnel 72. The injection port 30' can also be inserted through the first pathway 70, either manually or using an insertion tool, such as a port applier as disclosed in U.S. Publication No. 2006/0293626 of Byrum et al. filed on Jun. 24, 2005 and entitled " " and U.S. Publication No. 2006/0293627 of Byrum et al. and entitled "Applier For Safety With Implantable Medical Device," which are hereby incorporated by reference in their entireties. The sensor housing 60' and/or the injection port 30' could also be pulled into the pathway by retracting the catheter 50, e.g., by pulling on a portion of the catheter 50 disposed within the body cavity. The particular implant location of the injection port 30' can also vary, but in an exemplary embodiment the injection port 30' is positioned in the first pathway, preferably just offset from the first pathway 70 at least partially within tissue surrounding the first pathway 70. The injection port 30' can likewise be anchored to tissue using various anchoring techniques, such as sutures or other tissue engaging mechanisms. U.S. Publication No. 2005/0277899 of Conlon et al. filed on Jun. 1, 2004 and entitled "Method Of Implanting A Fluid Injection Port," which are hereby incorporated by reference in their entireties, disclose various embodiments of an injection port having tissue-engaging anchors formed on a distal surface thereof. A person skilled in the art will appreciate that various anchoring mechanisms can optionally be used, and the particular anchoring mechanism can depend on the particular configuration of the housing(s). With the sensor housing 60'and the injection port 30' implanted in tissue, the catheter 50' can extend from the housings to the gastric band 20'. The first pathway 70 can thus be closed, leaving the gastric restriction device 10' fully implanted.

While not shown, in another embodiment, rather than having the catheter 50 extend through the first pathway 70 and exit the skin incision, the catheter 50 could be fully disposed within the body cavity and a device inserted into the body cavity (e.g., the abdominal cavity) can be used to form an incision (e.g., through the peritoneum) and a second pathway extending into the tunnel 72. The second pathway does not necessarily need to extend out through a skin incision, it could be a fully internal pathway. The tunnel 72 will thus extend between the first pathway and the second pathway. The terminal end 50t of the catheter 50 can be inserted into the second pathway and grasped and pulled across the tunnel 72 and then removed through the first pathway 70 to allow the terminal end 50t of the catheter 50 to be mated to the housing(s). Once mated, the catheter 50 can be retracted to pull the housing(s) into the tunnel 72.

As indicated above, FIGS. 6-12B illustrate another exemplary embodiment of a method for implanting a device having at least one housing that is in-line with the gastric band, such as the device 10 of FIG. 1B. In this embodiment, a second pathway 74 is formed through a stomach wall, and it can extend to the fascia or all the way into the abdominal cavity. While not shown, the second pathway 74 can alternatively extend from the body cavity to the fascia, as explained above, to form an internal pathway. The second pathway 74 can be formed using various techniques, as previously explained with respect to the first pathway 70, and it can include an access device, such as a trocar, disposed therein and defining a working channel. In an exemplary embodiment, the second pathway 74 is positioned a distance apart from the first pathway 70. The distance can vary, but in certain exemplary embodiments the distance is in the range of about 10 cm to 20 cm.

Figure 7A:
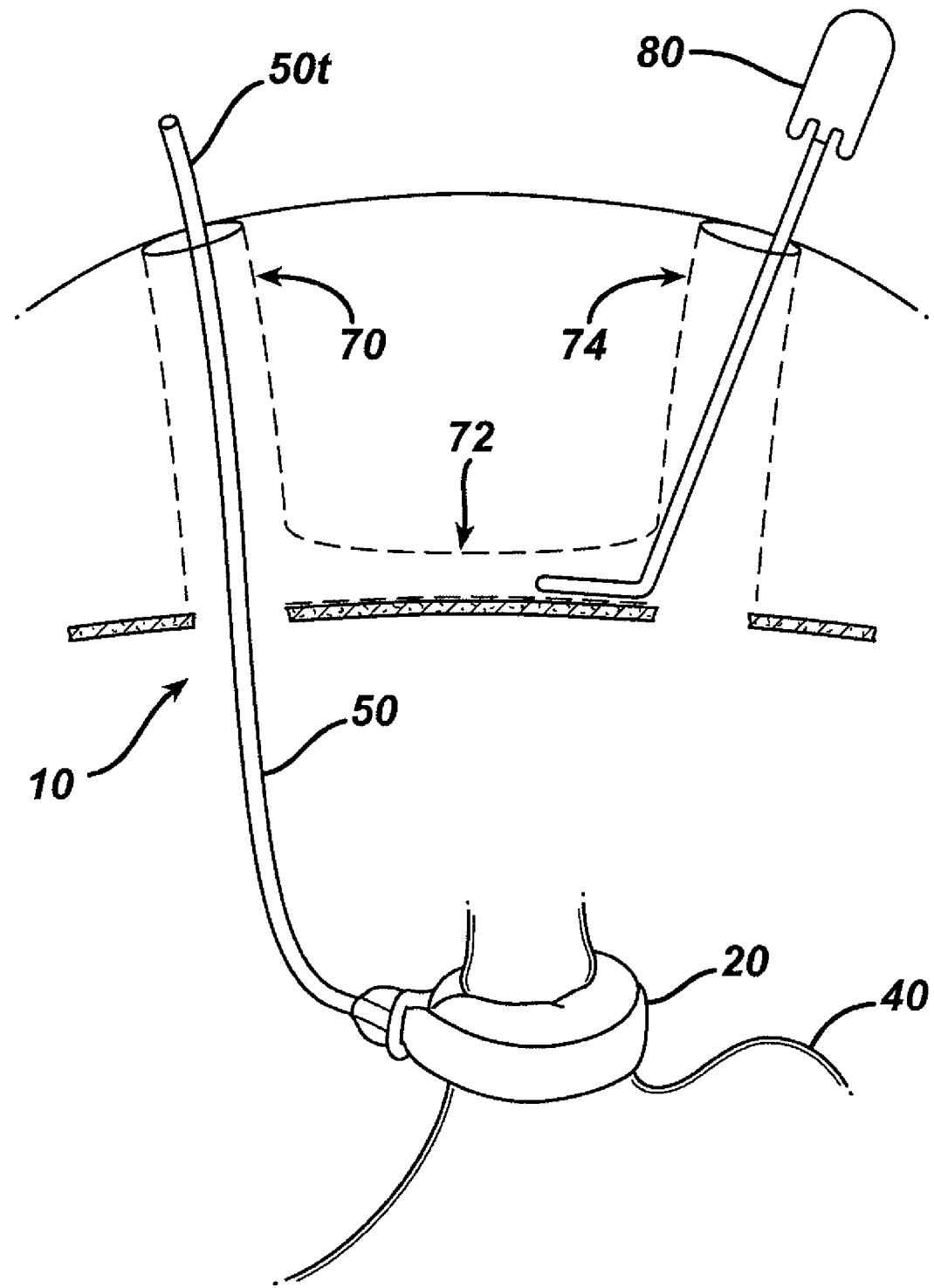
FIG. 7A is a side view illustration of the first and second pathways of FIG. 6, showing a tunnel being formed between the pathways using an elongate device.
Figure 7B:
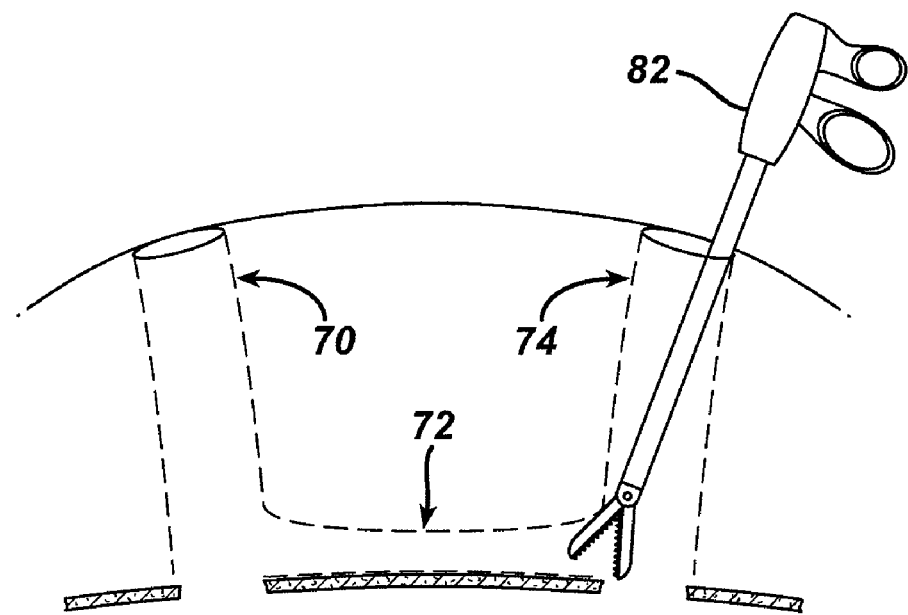
FIG. 7B is a side view illustration of the first and second pathways of FIG. 6, showing a tunnel being formed between the pathways using graspers.
Figure 7C:
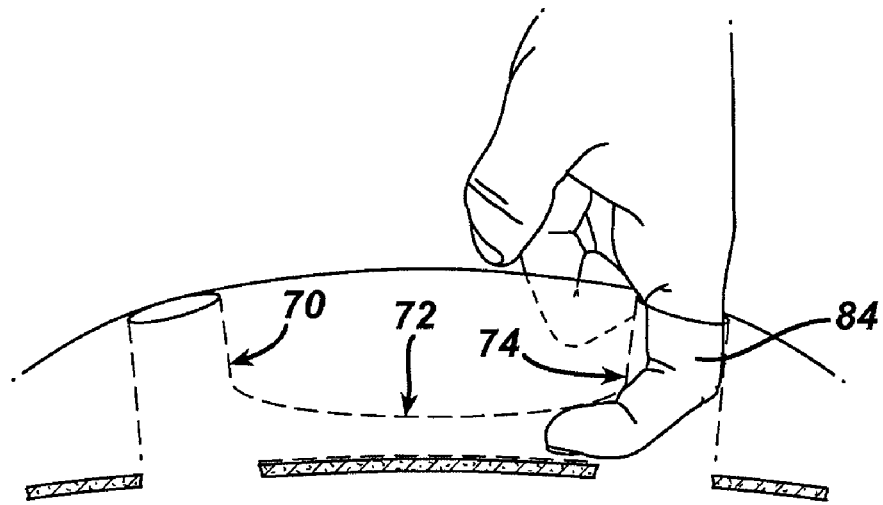
FIG. 7C is a side view illustration of the first and second pathways of FIG. 6, showing a tunnel being formed between the pathways using a finger.

Once the second pathway 74 is formed, a tunnel 72 can be formed between the first and second pathways 70, 74. As explained above, the particular direction and orientation of the tunnel 72 can vary, however as shown the tunnel 72 extends laterally between the first and second pathways 70, 74 in a direction transverse to a longitudinal axis of the pathways 70, 74. As a result, the tunnel 72 extends across the fascia layer, thus allowing at least one housing to be implanted and/or anchored to the fascia. The tunnel 72 can also be formed using various techniques, including those explained above with respect to FIGS. 3A-3C. Where the tunnel 72 extends between two pathways 70, 74, the tools and/or one's finger, can be inserted through one or both of the pathways 70, 74 to form a tunnel 72 extending between the two pathways 70, 74. FIGS. 7A illustrates the Goldfinger™ device inserted through the second pathway 74, FIG. 7B illustrates the graspers 82 inserted through the second pathway 74, and FIG. 7C illustrates a finger 84 inserted through the second pathway 74 for forming the tunnel 72. Again, a person skilled in the art will appreciate that various other techniques can be used to form a tunnel 72 extending between the first and second pathways 70, 74.

Figure 8A:
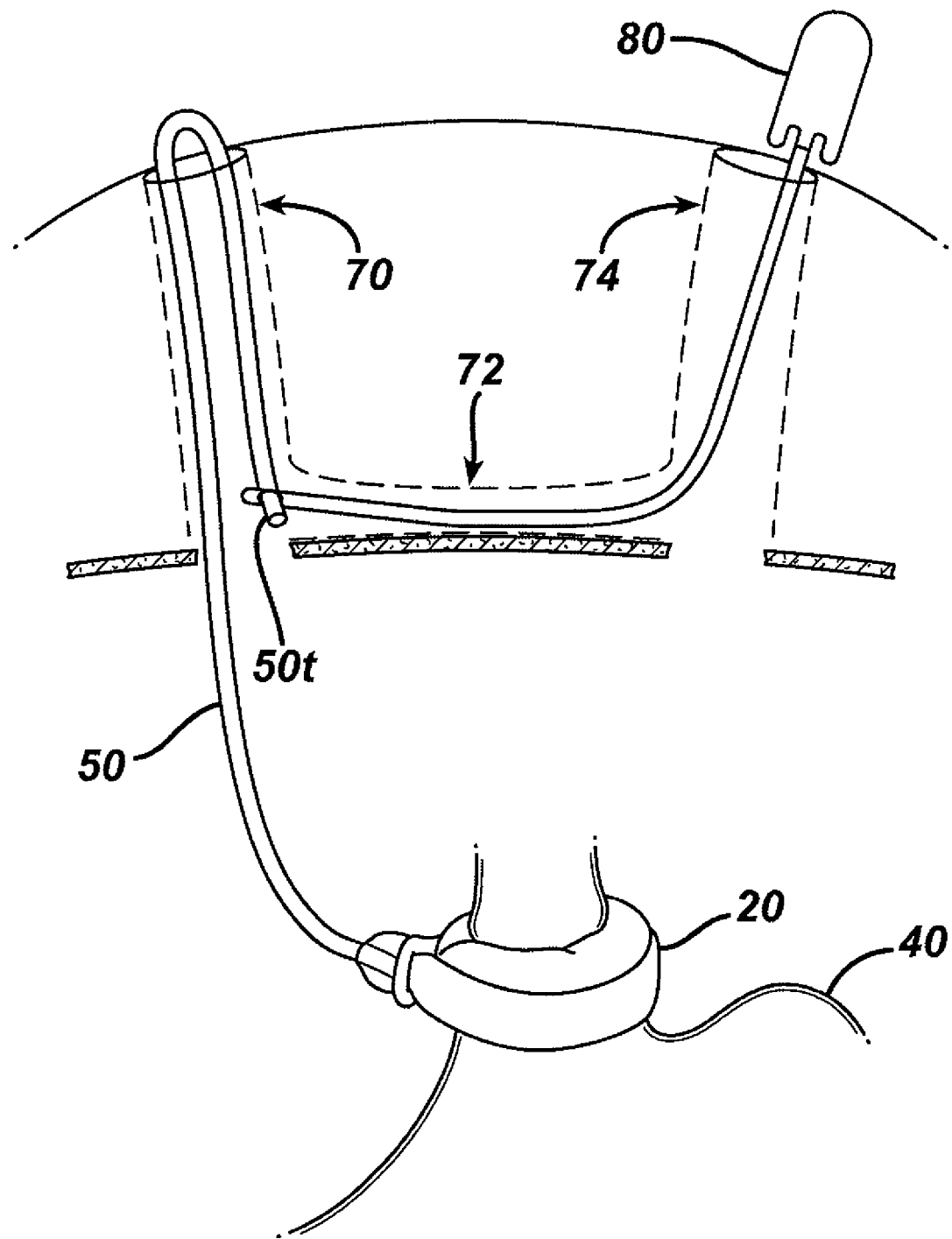
FIG. 8A is a side view illustration of the first and second pathways and the tunnel of FIGS. 7A-7C, showing an elongate device being used to grasp the catheter extending through the first pathway.
Figure 8B:
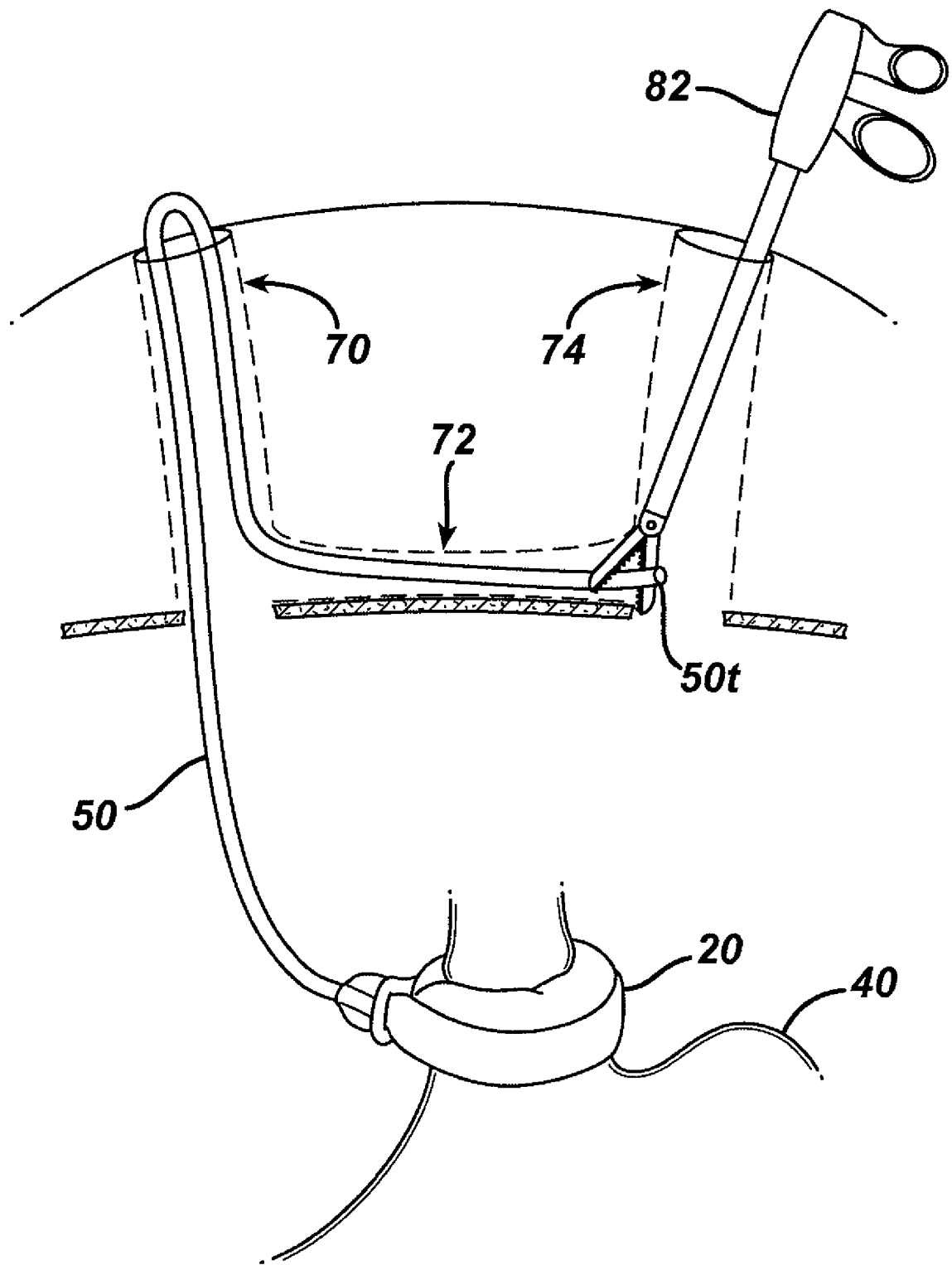
FIG. 8B is a side view illustration of the first and second pathways and the tunnel of FIGS. 7A-7C, showing graspers being used to grasp the catheter extending through the first pathway.
Figure 8C:
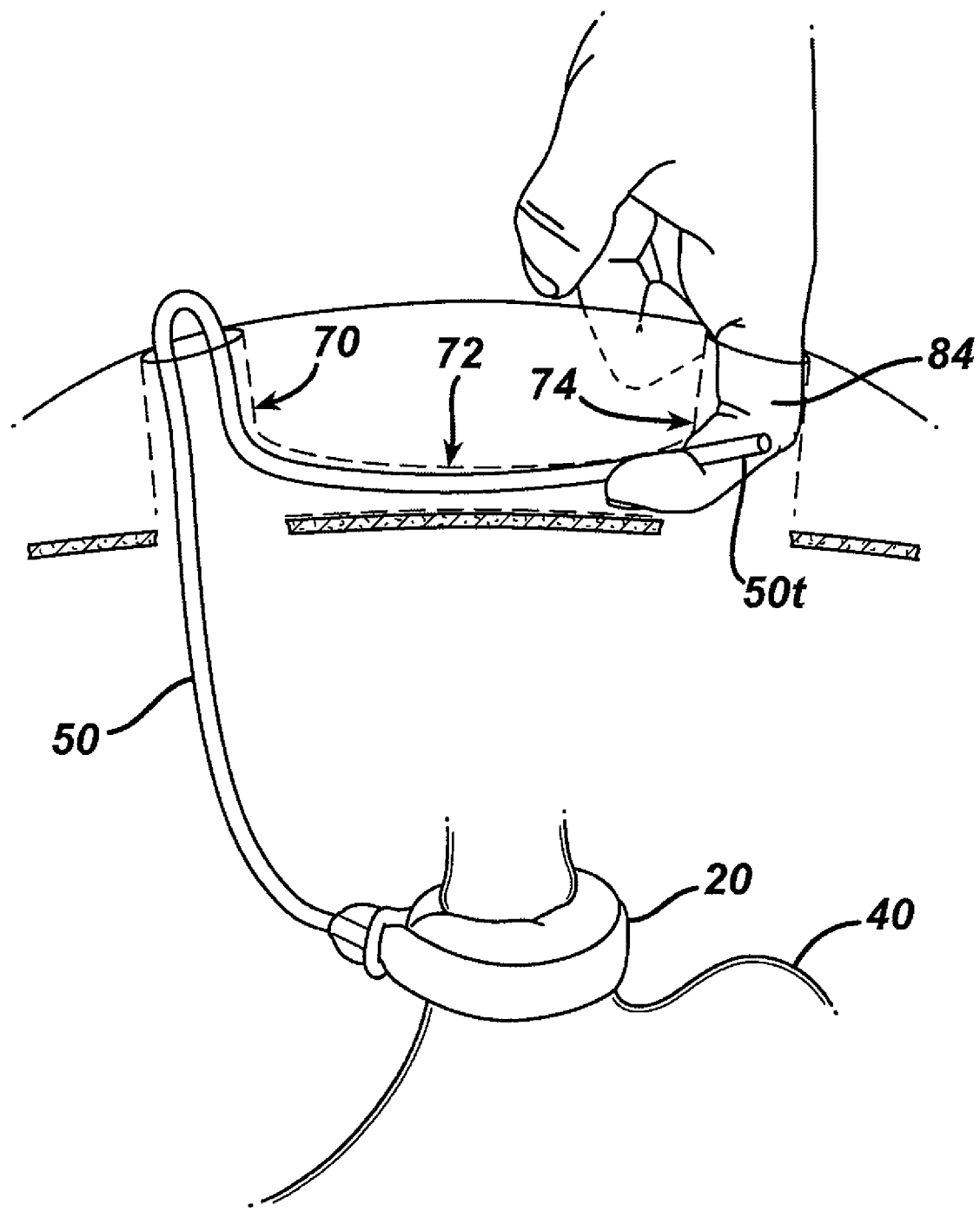
FIG. 8C is a side view illustration of the first and second pathways and the tunnel of FIGS. 7A-7C, showing a finger being used to grasp the catheter extending through the first pathway.
Figure 9:
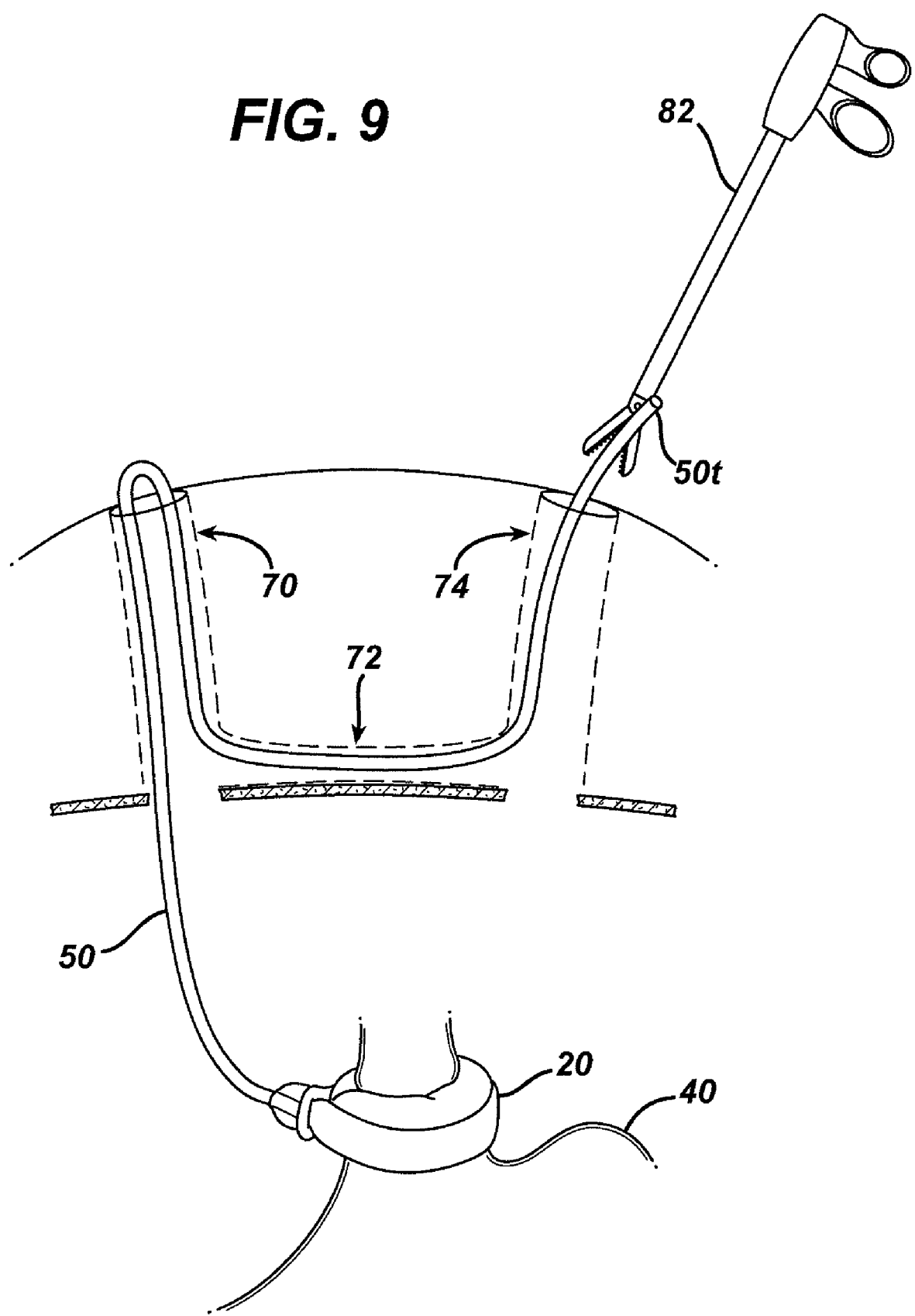
FIG. 9 is a side view illustration showing the graspers of FIG. 8B after pulling the catheter through the tunnel and out of the second pathway.
Figure 10:
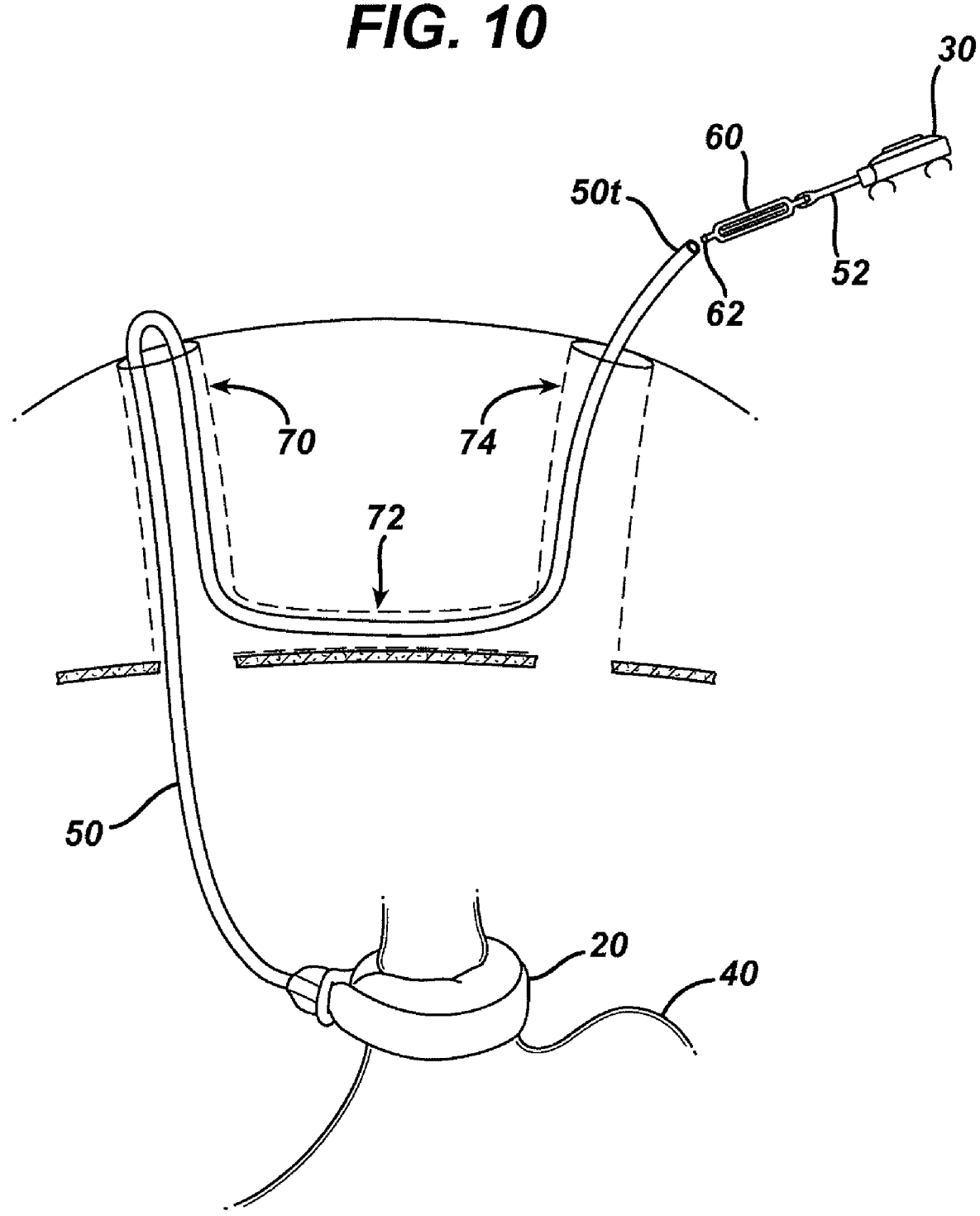
FIG. 10 is a side view illustration showing a terminal end of the catheter of FIG. 9 being coupled to a sensor housing which is coupled to an injection port.

Once the tunnel 72 is formed, in one embodiment the terminal end 50t of the catheter 50 can be advanced back into the first pathway 70 and pulled across the tunnel 72 and out of the second pathway 74 to exit through the skin incision. Various devices can be used to grasp and pull the terminal end 50t of the catheter 50 through the tunnel 72 and out of the second pathway 74. FIG. 8A illustrates the Goldfinger™ device 80 extending through the second pathway 74 and the tunnel 72, to grasp the terminal end 50t of the catheter 50 and thus pull it through the tunnel 72. FIG. 8B similarly illustrates the graspers 82 extending through the second pathway 74 and the tunnel 72 to grasp the terminal end 50t of the catheter 50, and FIG. 8C similarly illustrates a finger 84 extending through the second pathway 74 and the tunnel 72 to grasp the terminal end 50t of the catheter 50. Again, various other techniques can be used to advance and/or pull the terminal end 50t of the catheter 50 through the tunnel 72 and out of the second pathway 74. With the terminal end 50t of the catheter 50 extending from the second pathway 74, as shown in FIG. 9 which illustrates the graspers 82 engaging the terminal end 50t of the catheter, the terminal end 50t can be connected to one or more housings. As shown in FIG. 10, the terminal end 50t is about to be mated to the connector 62 on the sensor housing 60, which in turn is coupled to the injection port 30 via the connector 52. The sensor housing 60 and injection port 30 are thus in communication with the gastric band 20. Where the device 10 is a fluid-based device, the sensor housing 60 and injection port 30 are in fluid communication with the gastric band 20 when coupled, thus allowing the sensor housing 60 to measure, for example, the fluid pressure within the device 10, and allowing fluid to be introduced and/or removed through the injection port 30.

Figure 11:
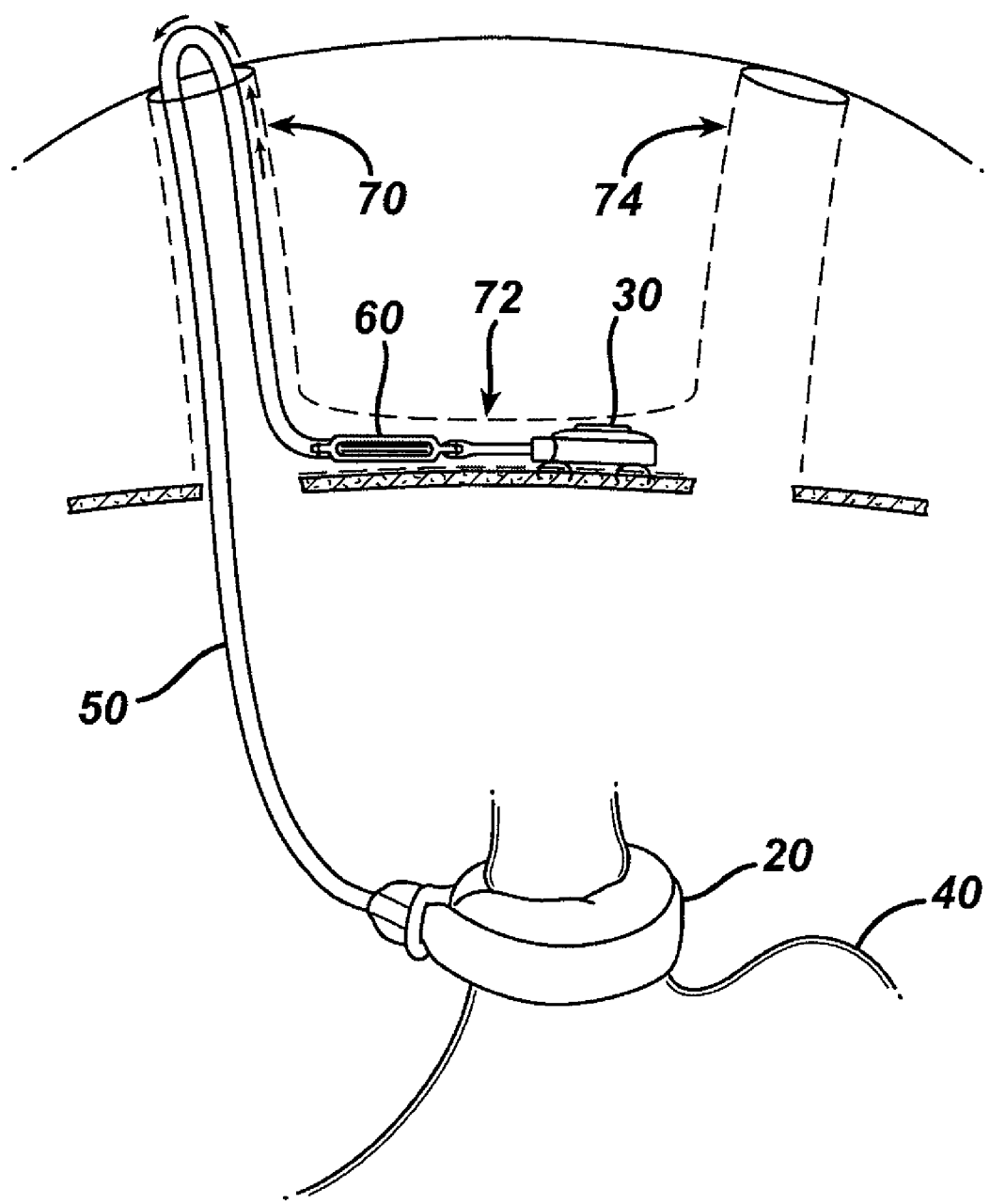
FIG. 11 is a side view illustration showing the catheter of FIG. 10 retracted into the tunnel to position the sensor housing and injection port within the tunnel.
Figure 12A:
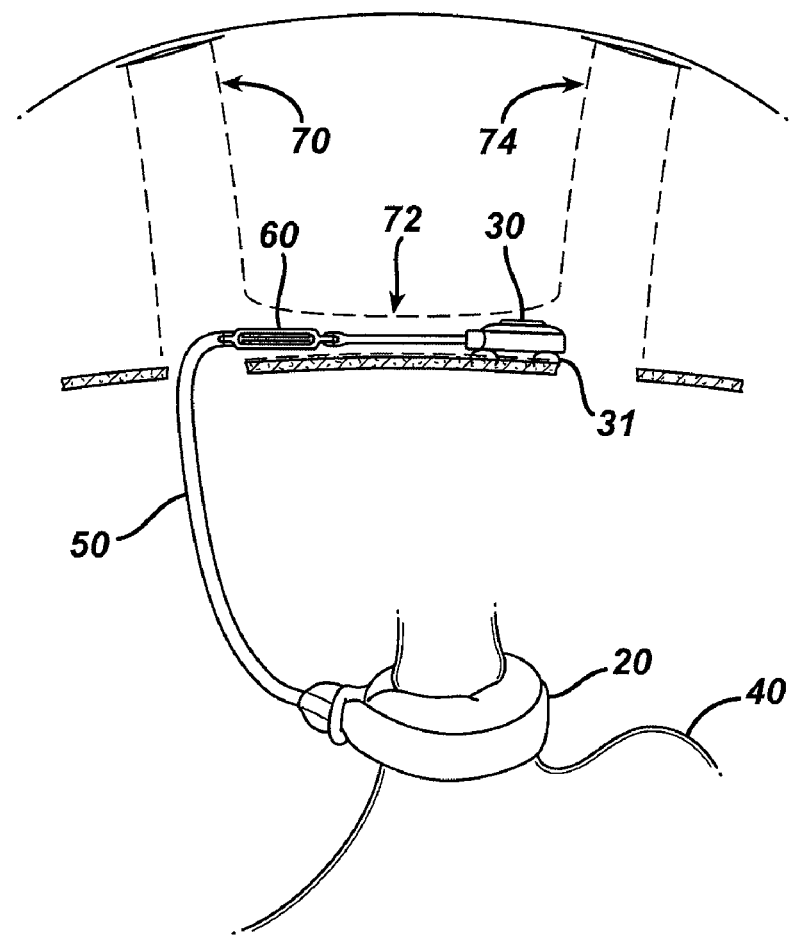
FIG. 12A is a side view of the sensor housing and injection port of FIG. 11 implanted in the tunnel, showing the sensor housing anchored to tissue.
Figure 12B:
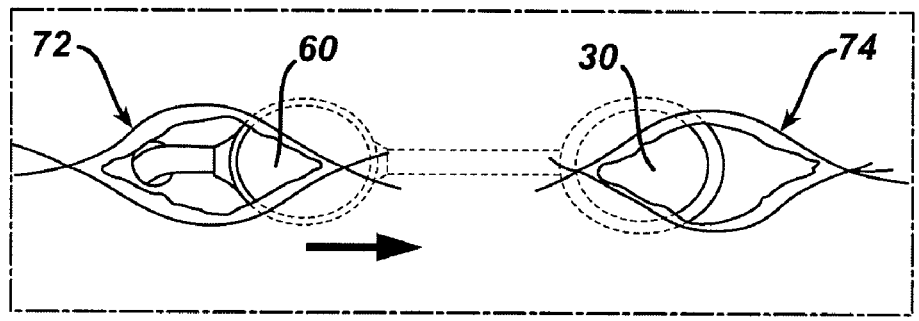
FIG. 12B is a top view of the sensor housing and injection port of FIG. 12A implanted in the tunnel.

Once connected, the catheter 50 can be retracted, for example, by pulling on the portion of the catheter 50 extending from the first pathway 70 and out through the skin incision, and/or by pulling on a portion of the catheter 50 disposed within the body cavity. This will pull the sensor housing 60 and injection port 30 into the second pathway 74 and into the tunnel 72, as shown in FIG. 11. Both housings can be fully disposed within the tunnel 72, or one or both housings can be positioned within or just adjacent to the pathways 70, 74. For example, as shown in FIG. 12A, the injection port 30 can be implanted within the second pathway 74 at a location offset from the longitudinal axis, i.e., in surrounding tissue or just at an entrance of the tunnel 72, and the sensor housing 60 can be implanted within the first pathway 70 at a location offset from the longitudinal axis, i.e., in surrounding tissue or just at an entrance of the tunnel 72. Such positioning can allow the injection port 30 and/or the sensor housing 60 to be anchored to tissue. By way of non-limiting example, FIG. 12A illustrates tissue-engaging members 31 on a distal surface of the injection port 30 engaging the fascia to retain the injection port 30 in a substantially fixed position. As previously explained, various other anchoring techniques can be used, if desired. While not shown, the sensor housing 60 can also optionally be anchored to tissue. FIG. 12B illustrates a top view of the device of FIG. 12A, showing the injection port 30 positioned adjacent to the second pathway 74 and the sensor housing 60 positioned adjacent to the first pathway 72.

In other embodiments, the terminal end 50t of the catheter 50 can be connected to one or more housings prior to being inserted through the first pathway 70 and advanced through the tunnel 72 to extend from the second pathway 74. For example, the terminal end 50t could be connected to a first housing, and the first housing, with the catheter attached thereto, could be inserted through the first pathway 70, across the tunnel 72, and through the second pathway 74 to exit the skin incision. One or more additional housings could then be coupled to the first housing and the catheter could be retracted to pull the additional housing(s) into the second pathway 74 and optionally into the tunnel 72. Alternatively, all housings could be coupled to the catheter prior to inserting the catheter through the first pathway 70 and into the tunnel 72. A person skilled in the art will appreciate that various techniques could be used, and the particular technique may depend on the particular configuration of the catheter.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a restriction system, comprising:
   forming a primary pathway through a skin incision;
   coupling a catheter exiting through the skin incision to a housing such that the housing is coupled, via the catheter, to a restriction device implanted to form a restriction;
   forming a tunnel extending from the primary pathway to a secondary pathway;
   positioning the housing within the tunnel;
   advancing the catheter from one of the primary pathway and the secondary pathway, through the tunnel, to the other one of the primary pathway and the secondary pathway; and
   coupling the catheter to the housing after advancing the catheter.

2. The method of claim 1, wherein the tunnel extends transverse to a longitudinal axis of the pathway.

3. The method of claim 1, wherein forming the tunnel comprises forming a finger tunnel.

4. The method of claim 1, wherein forming the tunnel comprises inserting an elongate member into the pathway and manipulating the elongate member to form a tunnel extending from the pathway.

5. The method of claim 1, wherein the tunnel is formed adjacent to a fascia layer.

6. The method of claim 1, wherein the housing comprises a first housing that is coupled to a second housing, and wherein the method further comprises positioning the second housing adjacent to the pathway.

7. The method of claim 1, wherein positioning the housing within the tunnel comprises retracting the catheter into the tunnel to pull the housing through one of the primary pathway and the secondary pathway and into the tunnel.

8. The method of claim 1, wherein the pathway extends from a skin incision and into a body cavity and the method further comprises advancing the restriction device through the pathway and into the body cavity.

9. The method of claim 1, wherein the housing is in fluid communication with the restriction device.

10. The method of claim 1, wherein the restriction device includes a sensor that measures at least one physiological parameter.

11. The method of claim 10, wherein the sensor comprises a pressure sensor.

12. A method for implanting a restriction system, comprising:
   advancing a restriction device through a pathway extending from a skin incision into a body cavity;

forming a single connection between a catheter coupled to the restriction device and one of a first housing and a second housing, the first and second housings being coupled to one another by a connector extending therebetween; and implanting the first and second housings in tissue, the first housing being implanted in a tunnel extending from the pathway and adjacent to a fascia layer, and the second housing being implanted in the pathway at an offset location.

13. The method of claim 12, wherein, when the restriction device is advanced through the pathway and into a body cavity, the catheter extends through the pathway and exits the skin incision.

14. The method of claim 12, wherein the pathway comprises a first pathway, and wherein the tunnel extends from the first pathway to a second pathway, and implanting the first and second housings comprises retracting the catheter into the tunnel.

15. The method of claim 14, wherein the catheter is advanced from the first pathway to the second pathway prior to forming a single connection between the catheter and one of the first and second housings.

16. The method of claim 12, wherein the tunnel is formed by advancing a finger through tissue adjacent to the pathway.

17. The method of claim 12, wherein the tunnel is formed by inserting an elongate member into the pathway and manipulating the elongate member to extend transverse to a longitudinal axis of the pathway.

18. A method of implanting a restriction system, comprising:

advancing a restriction device through a primary pathway extending from a skin incision to a body cavity to position the restriction device around an organ to be restricted;

forming a tunnel between the primary pathway and a secondary pathway;

advancing the trailing end of a catheter coupled to the restriction device through the primary pathway, across the tunnel, and through the secondary pathway such that the trailing end of the catheter exits the secondary pathway;

coupling the trailing end of the catheter to a housing; and implanting the housing in tissue;

wherein the trailing end of the catheter exits from the skin incision when the restriction device is advanced through the primary pathway.

19. The method of claim 18, wherein implanting the housing comprises retracting the catheter to position the housing within the tunnel, and implanting the housing in the tunnel.

20. The method of claim 19, wherein the catheter is retracted by pulling on a portion of the catheter extending from the primary pathway.

21. The method of claim 18, wherein the housing comprises a sensor housing that is coupled to a fill port, and wherein the method further comprises implanting the fill port in tissue.

* * * * *